(12) United States Patent
Solana

(10) Patent No.: US 11,998,504 B2
(45) Date of Patent: Jun. 4, 2024

(54) CHAIR INCLUDING PERCUSSIVE MASSAGE THERAPY

(71) Applicant: Therabody, Inc., Los Angeles, CA (US)

(72) Inventor: Jaime Sanchez Solana, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 17/931,079

(22) Filed: Sep. 9, 2022

(65) Prior Publication Data

US 2023/0079597 A1    Mar. 16, 2023

Related U.S. Application Data

(63) Continuation-in-part of application No. 17/833,412, filed on Jun. 6, 2022, now Pat. No. 11,813,221, which
(Continued)

(51) Int. Cl.
*A61H 23/00* (2006.01)
*A47C 1/00* (2006.01)
(Continued)

(52) U.S. Cl.
CPC ............ *A61H 23/006* (2013.01); *A47C 1/00* (2013.01); *A61H 7/007* (2013.01); *A61H 9/0078* (2013.01);
(Continued)

(58) Field of Classification Search
CPC ........ A61H 23/006; A61H 23/00; A61H 7/00; A61H 9/0078; A61H 2201/0165;
(Continued)

(56) References Cited

U.S. PATENT DOCUMENTS 657,765 A    9/1900  Gibbs
675,772 A    6/1901  Ferguson
(Continued)

FOREIGN PATENT DOCUMENTS

AT    510048 A1    1/2012
AU    2019204770 B1    10/2019
(Continued)

OTHER PUBLICATIONS

Machine translation of written description and claims for CN111973419A (Year: 2020).*
(Continued)

*Primary Examiner* — Michael R Reid
*Assistant Examiner* — Tyler A Raubenstraw
(74) *Attorney, Agent, or Firm* — Sterne, Kessler, Goldstein & Fox P.L.L.C.

(57) ABSTRACT

A massage chair includes a seat portion, a back portion a leg portion, and a massage carriage configured to move within the seat portion, the back portion, and the leg portion. The massage carriage includes comprises a percussive massage assembly comprising a motor, a reciprocating shaft coupled to the motor and configured to reciprocate in response to activation of the motor, and a reciprocating massage head coupled to the reciprocating shaft. The massage chair also includes a support mechanism associated with the percussive massage assembly. The support mechanism is configured to support a weight of a user of the massage chair, thereby allowing the reciprocating shaft and the reciprocating massage head of the percussive massage assembly to reciprocate.

19 Claims, 21 Drawing Sheets

Related U.S. Application Data is a continuation-in-part of application No. 17/515,008, filed on Oct. 29, 2021, now abandoned, which is a continuation of application No. 16/824,328, filed on Mar. 19, 2020, now Pat. No. 10,945,915, and a continuation of application No. 17/190,955, filed on Mar. 3, 2021, now Pat. No. 11,160,723, and a continuation-in-part of application No. 29/709,815, filed on Oct. 9, 2019, now Pat. No. Des. 951,470.

(60) Provisional application No. 63/242,621, filed on Sep. 10, 2021, provisional application No. 62/899,098, filed on Sep. 11, 2019, provisional application No. 62/844,424, filed on May 7, 2019.

(51) Int. Cl.
*A61H 7/00* (2006.01)
*A61H 9/00* (2006.01)
*A61N 5/06* (2006.01)

(52) U.S. Cl.
CPC ............... *A61H 2201/0149* (2013.01); *A61H 2201/0165* (2013.01); *A61H 2201/10* (2013.01); *A61H 2201/1215* (2013.01); *A61H 2201/1635* (2013.01); *A61H 2201/164* (2013.01); *A61H 2201/1669* (2013.01); *A61H 2201/1685* (2013.01); *A61H 2201/5025* (2013.01); *A61H 2203/0431* (2013.01); *A61H 2205/06* (2013.01); *A61H 2205/10* (2013.01); *A61N 2005/066* (2013.01)

(58) Field of Classification Search
CPC ............ A61H 7/007; A61H 2201/0149; A61H 2201/1215; A61H 2201/1669; A61H 2203/0431; A61H 2201/5025; A61H 2201/5007; A61H 2201/164; A61H 2201/1685; A61H 2205/06; A61H 2205/10; A47C 1/00; A47H 7/00; A61N 2005/066
See application file for complete search history.

(56) References Cited

U.S. PATENT DOCUMENTS

| | | |
|---|---|---|
| 1,545,027 A | 7/1925 | Ashlock |
| 1,594,636 A | 8/1926 | Smith |
| 1,657,765 A | 1/1928 | Pasque |
| 1,784,301 A | 12/1930 | Mekler |
| D91,454 S | 2/1934 | Decker |
| D93,943 S | 11/1934 | Harry |
| 2,179,594 A | 11/1939 | Johnson |
| D118,980 S | 2/1940 | Gilbert |
| D129,045 S | 8/1941 | Glenn |
| 2,391,671 A | 12/1945 | Berg |
| D143,678 S | 1/1946 | Snyder et al. |
| 2,475,861 A | 7/1949 | Alfred |
| D161,484 S | 1/1951 | Curtis |
| D163,324 S | 5/1951 | Charles |
| D180,923 S | 9/1957 | Nicholas |
| D181,742 S | 12/1957 | Alfred |
| 2,931,632 A | 4/1960 | De et al. |
| 2,987,334 A | 6/1961 | Wendling |
| 3,053,559 A | 9/1962 | Norval |
| 3,077,837 A | 2/1963 | Sidney et al. |
| D195,145 S | 4/1963 | Robert |
| D197,142 S | 12/1963 | James |
| 3,172,675 A | 3/1965 | Gonzalez |
| D207,505 S | 4/1967 | She |
| 3,452,226 A | 6/1969 | Hettich |
| 3,545,301 A | 12/1970 | Richter |
| 3,626,934 A | 12/1971 | Andis |
| 3,699,952 A | 10/1972 | Waters et al. |
| 3,705,579 A | 12/1972 | Morini et al. |
| D230,522 S | 2/1974 | Rothman |
| D237,454 S | 11/1975 | James |
| D237,455 S | 11/1975 | Buford |
| 3,942,251 A | 3/1976 | Griffies et al. |
| 3,968,789 A | 7/1976 | Simoncini |
| 4,031,763 A | 6/1977 | Eisenberg |
| 4,046,142 A | 9/1977 | Whitney |
| 4,088,128 A | 5/1978 | Mabuchi |
| 4,150,668 A | 4/1979 | Johnston |
| 4,158,246 A | 6/1979 | Meadows et al. |
| 4,173,217 A | 11/1979 | Johnston |
| 4,203,431 A | 5/1980 | Abura et al. |
| D265,985 S | 8/1982 | House, II |
| 4,506,159 A | 3/1985 | Reuter et al. |
| 4,513,737 A | 4/1985 | Mabuchi |
| 4,533,796 A | 8/1985 | Engelmore |
| 4,549,535 A | 10/1985 | Wing |
| 4,565,189 A | 1/1986 | Mabuchi |
| 4,566,442 A | 1/1986 | Mabuchi et al. |
| 4,596,406 A | 6/1986 | Van Vleet et al. |
| D287,814 S | 1/1987 | Hiraishi et al. |
| 4,691,693 A | 9/1987 | Sato |
| 4,692,958 A | 9/1987 | McMakin |
| D292,368 S | 10/1987 | Mikiya |
| 4,730,605 A | 3/1988 | Noble et al. |
| D300,132 S | 3/1989 | Culbertson et al. |
| 4,815,224 A | 3/1989 | Miller |
| 4,841,955 A | 6/1989 | Evans et al. |
| D303,373 S | 9/1989 | Ching, Jr. |
| D310,005 S | 8/1990 | Precht |
| D314,320 S | 2/1991 | Brosius et al. |
| 4,989,613 A | 2/1991 | Finkenberg |
| 4,991,298 A | 2/1991 | Matre |
| 5,014,681 A | 5/1991 | Neeman et al. |
| D320,379 S | 10/1991 | Culbertson |
| D321,338 S | 11/1991 | Sakamoto et al. |
| 5,085,207 A | 2/1992 | Fiore |
| 5,088,474 A | 2/1992 | Mabuchi et al. |
| 5,092,317 A | 3/1992 | Zelikovski |
| 5,103,809 A | 4/1992 | DeLuca et al. |
| 5,123,139 A | 6/1992 | Leppert et al. |
| D329,166 S | 9/1992 | Doggett |
| D329,291 S | 9/1992 | Wollman |
| D329,292 S | 9/1992 | Wollman |
| D331,467 S | 12/1992 | Wollman |
| D334,012 S | 3/1993 | Chen |
| 5,201,149 A | 4/1993 | Eisenblatter |
| 5,207,697 A | 5/1993 | Carusillo et al. |
| 5,212,887 A | 5/1993 | Farmerie |
| D338,802 S | 8/1993 | Maass |
| D345,077 S | 3/1994 | Maass |
| D345,727 S | 4/1994 | Flowers et al. |
| D345,888 S | 4/1994 | Joss et al. |
| D349,029 S | 7/1994 | Matsunaga et al. |
| 5,417,644 A | 5/1995 | Lee |
| D363,352 S | 10/1995 | Huen |
| D367,712 S | 3/1996 | Young |
| 5,501,657 A | 3/1996 | Feero |
| D374,934 S | 10/1996 | Lie |
| 5,569,168 A | 10/1996 | Hartwig |
| 5,573,500 A | 11/1996 | Katsunuma et al. |
| 5,656,017 A | 8/1997 | Keller et al. |
| 5,656,018 A | 8/1997 | Tseng |
| D383,366 S | 9/1997 | Heck |
| D383,435 S | 9/1997 | Svetlik |
| D384,639 S | 10/1997 | Kawakami et al. |
| D387,728 S | 12/1997 | Kawakami et al. |
| D388,175 S | 12/1997 | Lie |
| D397,991 S | 9/1998 | Kawakami et al. |
| D400,161 S | 10/1998 | Nagele et al. |
| D400,758 S | 11/1998 | Hippen et al. |
| 5,860,669 A | 1/1999 | Wass et al. |
| D408,543 S | 4/1999 | Back |
| 5,910,197 A | 6/1999 | Chaconas |
| 5,925,002 A | 7/1999 | Wollman |
| D412,485 S | 8/1999 | Kato et al. |
| 5,935,089 A | 8/1999 | Shimizu |
| 5,951,501 A | 9/1999 | Griner |

(56) References Cited

U.S. PATENT DOCUMENTS

| | | |
|---|---|---|
| D417,648 S | 12/1999 | Clowers et al. |
| 6,003,052 A | 12/1999 | Yamagata |
| 6,006,631 A | 12/1999 | Miner et al. |
| D425,014 S | 5/2000 | Willkens et al. |
| D430,774 S | 9/2000 | Naft et al. |
| D430,938 S | 9/2000 | Lee |
| D432,077 S | 10/2000 | Zurwelle et al. |
| D433,300 S | 11/2000 | Buck |
| 6,146,383 A | 11/2000 | Studer et al. |
| 6,165,145 A | 12/2000 | Noble |
| D439,984 S | 4/2001 | Thach |
| D440,136 S | 4/2001 | Buck |
| 6,227,959 B1 | 5/2001 | Beaudry |
| 6,228,042 B1 | 5/2001 | Dungan |
| 6,228,120 B1 | 5/2001 | Leonard et al. |
| 6,245,031 B1 | 6/2001 | Pearson |
| 6,290,660 B1 | 9/2001 | Epps et al. |
| D448,852 S | 10/2001 | Engelen |
| 6,401,289 B1 | 6/2002 | Herbert |
| 6,406,445 B1 | 6/2002 | Ben-Nun |
| 6,432,072 B1 | 8/2002 | Harris et al. |
| 6,537,236 B2 | 3/2003 | Tucek et al. |
| 6,539,328 B1 | 3/2003 | Cremonese et al. |
| D474,445 S | 5/2003 | Matsuoka et al. |
| 6,558,338 B1 | 5/2003 | Wasserman |
| 6,568,089 B1 | 5/2003 | Popik et al. |
| D475,595 S | 6/2003 | Hatch et al. |
| D475,679 S | 6/2003 | Cooper et al. |
| D476,746 S | 7/2003 | Harris et al. |
| 6,599,250 B2 | 7/2003 | Webb et al. |
| 6,599,260 B2 | 7/2003 | Tucek et al. |
| D478,385 S | 8/2003 | Dirks et al. |
| D481,279 S | 10/2003 | Buck |
| 6,663,657 B1 | 12/2003 | Miller |
| 6,682,496 B1 | 1/2004 | Pivaroff |
| 6,715,781 B1 | 4/2004 | Smith |
| 6,723,050 B2 | 4/2004 | Dow et al. |
| 6,723,060 B2 | 4/2004 | Miller |
| 6,758,826 B2 | 7/2004 | Luettgen et al. |
| 6,805,700 B2 | 10/2004 | Miller |
| 6,823,762 B2 | 11/2004 | Hu |
| 6,846,295 B1 | 1/2005 | Ben-Nun |
| D504,111 S | 4/2005 | Ozawa et al. |
| D510,317 S | 10/2005 | Sun |
| 6,994,575 B1 | 2/2006 | Clark et al. |
| 7,041,072 B2 | 5/2006 | Calvert |
| D530,270 S | 10/2006 | Ozawa et al. |
| 7,128,721 B2 | 10/2006 | Ferber et al. |
| D531,733 S | 11/2006 | Burout, III et al. |
| 7,169,169 B2 | 1/2007 | Tucek et al. |
| 7,223,250 B2 | 5/2007 | Brattesani et al. |
| D544,102 S | 6/2007 | Pivaroff |
| D544,436 S | 6/2007 | Kawahara et al. |
| D547,264 S | 7/2007 | Kondo |
| D553,252 S | 10/2007 | Masuda |
| D553,562 S | 10/2007 | Okada et al. |
| 7,384,405 B2 | 6/2008 | Rhoades |
| D575,224 S | 8/2008 | Taniguchi et al. |
| 7,431,706 B2 | 10/2008 | Louis |
| D579,868 S | 11/2008 | Harrison |
| D580,353 S | 11/2008 | Harrison et al. |
| 7,470,081 B2 | 12/2008 | Miyahara et al. |
| D587,977 S | 3/2009 | Waldron |
| 7,497,639 B2 | 3/2009 | Lebot et al. |
| 7,503,923 B2 | 3/2009 | Miller |
| D593,204 S | 5/2009 | Manke et al. |
| 7,549,966 B2 * | 6/2009 | Fujii ............... A61H 15/0078 601/149 |
| D597,482 S | 8/2009 | Kondo et al. |
| D604,235 S | 11/2009 | Tarter |
| D605,586 S | 12/2009 | Tong |
| D606,192 S | 12/2009 | Summerer et al. |
| 7,731,672 B2 * | 6/2010 | Chiang ............... A61H 15/00 601/103 |
| 7,740,249 B1 | 6/2010 | Gao |
| D622,660 S | 8/2010 | Taniguchi et al. |
| 7,857,729 B2 | 12/2010 | Sullivan et al. |
| D631,315 S | 1/2011 | Xue et al. |
| 7,877,880 B2 | 2/2011 | Royle |
| 7,927,259 B1 | 4/2011 | Rix |
| 7,927,294 B2 | 4/2011 | Kamimura et al. |
| 7,963,717 B2 | 6/2011 | Seger |
| 7,996,996 B2 | 8/2011 | Hirabayashi |
| D649,657 S | 11/2011 | Petersen et al. |
| D658,759 S | 5/2012 | Marescaux et al. |
| D659,644 S | 5/2012 | Gretz |
| D666,303 S | 8/2012 | Ding et al. |
| 8,313,450 B2 | 11/2012 | Ben-Nun |
| 8,342,187 B2 | 1/2013 | Kalman et al. |
| D682,195 S | 5/2013 | Aglassinger |
| 8,435,194 B2 | 5/2013 | Dverin et al. |
| 8,479,616 B2 | 7/2013 | Tsai |
| 8,622,943 B2 | 1/2014 | Ben-Nun |
| 8,646,348 B2 | 2/2014 | Hung |
| D703,337 S | 4/2014 | Fuhr et al. |
| D703,480 S | 4/2014 | Lownds |
| 8,695,461 B2 | 4/2014 | Moss et al. |
| D706,433 S | 6/2014 | Fuhr et al. |
| D708,742 S | 7/2014 | Dallemagne et al. |
| 8,770,882 B2 | 7/2014 | Ersoy |
| 8,777,881 B2 | 7/2014 | Tsai |
| 8,864,143 B2 | 10/2014 | Lin |
| D722,016 S | 2/2015 | Beukema |
| 8,945,104 B2 | 2/2015 | Boone, III et al. |
| 8,951,216 B2 | 2/2015 | Yoo et al. |
| D726,495 S | 4/2015 | Ryan |
| 9,017,273 B2 * | 4/2015 | Burbank ............ A61H 23/0218 601/46 |
| D734,863 S | 7/2015 | Hennessey |
| D735,348 S | 7/2015 | Hennessey |
| 9,107,486 B2 | 8/2015 | Brewer et al. |
| 9,132,058 B2 | 9/2015 | Imboden et al. |
| 9,138,257 B2 | 9/2015 | Revivo |
| D740,222 S | 10/2015 | Tang |
| 9,272,837 B2 | 3/2016 | Linzell |
| D756,180 S | 5/2016 | Chen |
| D759,237 S | 6/2016 | Heath et al. |
| D759,238 S | 6/2016 | Heath et al. |
| 9,364,385 B2 * | 6/2016 | Yang ..................... A61H 7/007 |
| D763,442 S | 8/2016 | Price et al. |
| 9,416,805 B2 | 8/2016 | Cascolan et al. |
| D776,612 S | 1/2017 | Chen et al. |
| D778,439 S | 2/2017 | Håkansson et al. |
| 9,597,256 B1 | 3/2017 | Paul |
| 9,744,600 B2 | 8/2017 | Yang et al. |
| 9,872,813 B2 | 1/2018 | Giraud et al. |
| 9,889,066 B2 | 2/2018 | Danby et al. |
| D817,732 S | 5/2018 | Rettler |
| D817,869 S | 5/2018 | Lee et al. |
| D819,221 S | 5/2018 | Lei |
| 9,981,366 B2 | 5/2018 | Todd et al. |
| D823,478 S | 7/2018 | Park |
| 10,034,813 B1 * | 7/2018 | Silver .................... A61H 7/007 |
| D826,418 S | 8/2018 | Lad |
| D837,395 S | 1/2019 | Gan |
| D838,378 S | 1/2019 | Cao |
| D840,547 S | 2/2019 | Harle et al. |
| 10,201,470 B2 | 2/2019 | Griner |
| D842,489 S | 3/2019 | Spewock et al. |
| D842,491 S | 3/2019 | Fleming et al. |
| D843,656 S | 3/2019 | Zhang et al. |
| D844,896 S | 4/2019 | Levi et al. |
| D847,362 S | 4/2019 | Tang |
| D847,364 S | 4/2019 | Lee et al. |
| 10,252,051 B2 | 4/2019 | Nichols |
| 10,276,844 B2 | 4/2019 | Wackwitz et al. |
| D847,990 S | 5/2019 | Kimball |
| 10,314,762 B1 | 6/2019 | Marton et al. |
| 10,335,345 B2 | 7/2019 | Choe |
| 10,357,425 B2 | 7/2019 | Wersland et al. |
| D855,822 S | 8/2019 | Marton et al. |
| D858,432 S | 9/2019 | Altenburger |
| D862,382 S | 10/2019 | Altenburger |
| D866,790 S | 11/2019 | Lee et al. |

(56) References Cited

U.S. PATENT DOCUMENTS

| | | | |
|---|---|---|---|
| D867,279 S | 11/2019 | Altenburger | |
| 10,557,490 B2 | 2/2020 | Wersland et al. | |
| D877,351 S | 3/2020 | Wersland et al. | |
| D880,419 S | 4/2020 | Hernandez et al. | |
| D880,714 S | 4/2020 | Wersland et al. | |
| D880,715 S | 4/2020 | Wersland et al. | |
| D880,716 S | 4/2020 | Wersland et al. | |
| D884,205 S | 5/2020 | Zhuang | |
| 10,702,448 B2 | 7/2020 | Wersland et al. | |
| D893,738 S | 8/2020 | Zhuang | |
| 10,758,027 B2* | 9/2020 | Skidmore | A45D 34/04 |
| 10,857,064 B2 | 12/2020 | Wersland et al. | |
| 10,918,565 B2 | 2/2021 | Wersland et al. | |
| 10,945,915 B2 | 3/2021 | Wersland et al. | |
| 10,959,908 B2 | 3/2021 | Lee et al. | |
| 10,959,911 B2 | 3/2021 | Wersland et al. | |
| D919,560 S | 5/2021 | Taniguchi et al. | |
| 10,993,874 B1 | 5/2021 | Marton et al. | |
| 11,160,723 B2 | 11/2021 | Wersland et al. | |
| 11,452,667 B2* | 9/2022 | Tan | A47C 7/40 |
| 11,478,400 B1 | 10/2022 | Marton et al. | |
| 2001/0016697 A1 | 8/2001 | Gorsen | |
| 2001/0027280 A1 | 10/2001 | Huang | |
| 2002/0082532 A1 | 6/2002 | Tucek et al. | |
| 2002/0115947 A1 | 8/2002 | Young | |
| 2002/0177795 A1 | 11/2002 | Frye | |
| 2002/0183668 A1 | 12/2002 | Huang | |
| 2002/0188233 A1 | 12/2002 | Denyes | |
| 2003/0009116 A1 | 1/2003 | Luettgen et al. | |
| 2003/0014079 A1 | 1/2003 | Tucek | |
| 2003/0028134 A1 | 2/2003 | Lev et al. | |
| 2003/0094356 A1 | 5/2003 | Waldron | |
| 2003/0144615 A1 | 7/2003 | Lin | |
| 2003/0195443 A1 | 10/2003 | Miller | |
| 2004/0176710 A1 | 9/2004 | Kennedy et al. | |
| 2005/0075591 A1 | 4/2005 | Hafemann | |
| 2005/0109137 A1 | 5/2005 | Hartmann | |
| 2005/0113870 A1 | 5/2005 | Miller | |
| 2005/0126018 A1 | 6/2005 | Haas | |
| 2005/0131461 A1 | 6/2005 | Tucek et al. | |
| 2005/0203445 A1 | 9/2005 | Tsai | |
| 2005/0235988 A1 | 10/2005 | Hansen et al. | |
| 2005/0252011 A1 | 11/2005 | Neumeier | |
| 2006/0025710 A1 | 2/2006 | Schulz et al. | |
| 2006/0047315 A1 | 3/2006 | Colloca et al. | |
| 2006/0074455 A1 | 4/2006 | Strandberg | |
| 2006/0116614 A1 | 6/2006 | Jones et al. | |
| 2006/0118841 A1 | 6/2006 | Eliason et al. | |
| 2006/0123941 A1 | 6/2006 | Wadge | |
| 2006/0192527 A1 | 8/2006 | Kageler et al. | |
| 2006/0211961 A1 | 9/2006 | Meyer et al. | |
| 2006/0272664 A1 | 12/2006 | O'Dwyer | |
| 2007/0055186 A1* | 3/2007 | Hsieh | A61H 15/0078 |
| | | | 601/99 |
| 2007/0129220 A1 | 6/2007 | Bardha | |
| 2007/0144310 A1 | 6/2007 | Pozgay et al. | |
| 2007/0150004 A1 | 6/2007 | Colloca et al. | |
| 2007/0173886 A1 | 7/2007 | Rousso et al. | |
| 2007/0179414 A1 | 8/2007 | Imboden et al. | |
| 2007/0270727 A1 | 11/2007 | Khorassani Zadeh | |
| 2007/0282228 A1 | 12/2007 | Einav et al. | |
| 2008/0077061 A1* | 3/2008 | Dehli | A61H 23/02 |
| | | | 601/134 |
| 2008/0097260 A1 | 4/2008 | Tsukada et al. | |
| 2008/0103419 A1 | 5/2008 | Adamson | |
| 2008/0146980 A1* | 6/2008 | Rousso | A61H 7/001 |
| | | | 601/152 |
| 2008/0167588 A1 | 7/2008 | Chen | |
| 2008/0169715 A1 | 7/2008 | Mills et al. | |
| 2008/0177207 A1 | 7/2008 | Liao | |
| 2008/0185888 A1 | 8/2008 | Beall et al. | |
| 2008/0200849 A1 | 8/2008 | Hollington et al. | |
| 2008/0243041 A1 | 10/2008 | Brenner et al. | |
| 2008/0306417 A1 | 12/2008 | Imboden et al. | |
| 2008/0312568 A1* | 12/2008 | Chen | A61H 15/0078 |
| | | | 601/126 |
| 2008/0314610 A1 | 12/2008 | Meixner | |
| 2009/0112134 A1 | 4/2009 | Avni | |
| 2009/0188119 A1 | 7/2009 | Oberheim | |
| 2009/0270777 A1* | 10/2009 | Wu | A61H 7/007 |
| | | | 601/87 |
| 2009/0309313 A1 | 12/2009 | Knorr et al. | |
| 2009/0326540 A1 | 12/2009 | Estes | |
| 2010/0100119 A1 | 4/2010 | Herndon | |
| 2010/0137907 A1 | 6/2010 | Tsai | |
| 2010/0145242 A1 | 6/2010 | Tsai | |
| 2010/0160841 A1 | 6/2010 | Wu | |
| 2010/0162579 A1 | 7/2010 | Naughton et al. | |
| 2010/0176919 A1 | 7/2010 | Myers et al. | |
| 2010/0210194 A1 | 8/2010 | Thomaschewski et al. | |
| 2010/0274162 A1 | 10/2010 | Evans | |
| 2010/0286569 A1* | 11/2010 | Nagano | A61H 1/008 |
| | | | 601/84 |
| 2010/0298863 A1 | 11/2010 | Hindinger et al. | |
| 2011/0037431 A1 | 2/2011 | Mackle | |
| 2011/0055720 A1 | 3/2011 | Potter et al. | |
| 2011/0118637 A1 | 5/2011 | Lev et al. | |
| 2011/0201979 A1 | 8/2011 | Voss et al. | |
| 2011/0224580 A1 | 9/2011 | Leathers et al. | |
| 2011/0314677 A1 | 12/2011 | Meier et al. | |
| 2012/0059294 A1 | 3/2012 | Schubert et al. | |
| 2012/0065556 A1 | 3/2012 | Smith et al. | |
| 2012/0078071 A1 | 3/2012 | Bohm et al. | |
| 2012/0124758 A1 | 5/2012 | Sabisch et al. | |
| 2012/0161706 A1 | 6/2012 | Zhou | |
| 2012/0197357 A1 | 8/2012 | Dewey et al. | |
| 2012/0232445 A1 | 9/2012 | Lev et al. | |
| 2012/0238922 A1 | 9/2012 | Stemple et al. | |
| 2012/0253245 A1 | 10/2012 | Stanbridge | |
| 2013/0014968 A1 | 1/2013 | Kehoe et al. | |
| 2013/0030506 A1 | 1/2013 | Bartolone et al. | |
| 2013/0046212 A1 | 2/2013 | Nichols | |
| 2013/0052871 A1 | 2/2013 | Eklind | |
| 2013/0085421 A1 | 4/2013 | Gillespie et al. | |
| 2013/0116503 A1 | 5/2013 | Mertens et al. | |
| 2013/0133210 A1 | 5/2013 | Weir et al. | |
| 2013/0138023 A1 | 5/2013 | Lerro | |
| 2013/0218058 A1 | 8/2013 | Ceoldo et al. | |
| 2013/0237751 A1 | 9/2013 | Alexander | |
| 2013/0241470 A1 | 9/2013 | Kim | |
| 2013/0261516 A1 | 10/2013 | Cilea et al. | |
| 2013/0261517 A1 | 10/2013 | Rodgers | |
| 2013/0271067 A1 | 10/2013 | Yu et al. | |
| 2013/0281897 A1 | 10/2013 | Hoffmann et al. | |
| 2013/0304642 A1 | 11/2013 | Campos | |
| 2014/0024982 A1 | 1/2014 | Doyle | |
| 2014/0031866 A1 | 1/2014 | Fuhr et al. | |
| 2014/0097793 A1 | 4/2014 | Wurtz et al. | |
| 2014/0101872 A1 | 4/2014 | Utsch et al. | |
| 2014/0163443 A1 | 6/2014 | Young et al. | |
| 2014/0180331 A1 | 6/2014 | Turner | |
| 2014/0190023 A1 | 7/2014 | Vitantonio et al. | |
| 2014/0194900 A1 | 7/2014 | Sedic | |
| 2014/0200495 A1 | 7/2014 | Jones | |
| 2014/0207032 A1 | 7/2014 | Dematio et al. | |
| 2014/0209594 A1* | 7/2014 | Besner | A61F 7/007 |
| | | | 219/217 |
| 2014/0221887 A1 | 8/2014 | Wu | |
| 2014/0288473 A1 | 9/2014 | Matsushita | |
| 2014/0305747 A1 | 10/2014 | Kumar et al. | |
| 2014/0310900 A1 | 10/2014 | Curry et al. | |
| 2014/0316313 A1 | 10/2014 | Mayer et al. | |
| 2015/0005682 A1 | 1/2015 | Danby et al. | |
| 2015/0042254 A1 | 2/2015 | Kato | |
| 2015/0082562 A1 | 3/2015 | Kamada | |
| 2015/0098184 A1 | 4/2015 | Tsai et al. | |
| 2015/0119771 A1 | 4/2015 | Roberts | |
| 2015/0133833 A1 | 5/2015 | Bradley et al. | |
| 2015/0145297 A1* | 5/2015 | Lee | B60N 2/2887 |
| | | | 297/219.1 |
| 2015/0148592 A1 | 5/2015 | Kanbar et al. | |
| 2015/0157528 A1* | 6/2015 | Le | A61H 23/006 |
| | | | 601/99 |

(56) References Cited

U.S. PATENT DOCUMENTS

| | | |
|---|---|---|
| 2015/0176674 A1 | 6/2015 | Khan et al. |
| 2015/0216719 A1 | 8/2015 | DeBenedictis et al. |
| 2015/0257964 A1 | 9/2015 | Ajiki |
| 2015/0305969 A1 | 10/2015 | Giraud et al. |
| 2015/0328081 A1 | 11/2015 | Goldenberg et al. |
| 2015/0375315 A1 | 12/2015 | Ukai et al. |
| 2016/0000642 A1* | 1/2016 | Zipper .................. A61H 19/34 600/38 |
| 2016/0017905 A1 | 1/2016 | Cascolan et al. |
| 2016/0030279 A1 | 2/2016 | Driscoll et al. |
| 2016/0045661 A1 | 2/2016 | Gray et al. |
| 2016/0112841 A1 | 4/2016 | Holland |
| 2016/0113840 A1 | 4/2016 | Crunick et al. |
| 2016/0113841 A1 | 4/2016 | Godfrey et al. |
| 2016/0127129 A1 | 5/2016 | Chee et al. |
| 2016/0129186 A1 | 5/2016 | Douglas et al. |
| 2016/0136037 A1 | 5/2016 | Cai |
| 2016/0136040 A1 | 5/2016 | Li |
| 2016/0166464 A1 | 6/2016 | Douglas et al. |
| 2016/0170996 A1 | 6/2016 | Frank et al. |
| 2016/0192814 A1 | 7/2016 | Kang et al. |
| 2016/0206502 A1 | 7/2016 | Køltzow |
| 2016/0243359 A1 | 8/2016 | Sharma |
| 2016/0263732 A1 | 9/2016 | Lourenco et al. |
| 2016/0269486 A1 | 9/2016 | Gupta et al. |
| 2016/0310353 A1 | 10/2016 | Barasch |
| 2016/0311091 A1 | 10/2016 | Wang |
| 2016/0324717 A1 | 11/2016 | Burton |
| 2016/0338901 A1 | 11/2016 | Cohen |
| 2016/0346163 A1 | 12/2016 | Konik et al. |
| 2016/0367425 A1 | 12/2016 | Wersland |
| 2017/0027798 A1 | 2/2017 | Wersland |
| 2017/0042754 A1 | 2/2017 | Fowers et al. |
| 2017/0049278 A1 | 2/2017 | Thomassen |
| 2017/0069191 A1 | 3/2017 | Erkkila |
| 2017/0119623 A1 | 5/2017 | Attarian |
| 2017/0128320 A1* | 5/2017 | Chen .................. A61H 15/0078 |
| 2017/0156974 A1 | 6/2017 | Griner |
| 2017/0156975 A1 | 6/2017 | Mills |
| 2017/0189227 A1 | 7/2017 | Brunson et al. |
| 2017/0216136 A1 | 8/2017 | Gordon |
| 2017/0233063 A1 | 8/2017 | Zhao et al. |
| 2017/0246074 A1* | 8/2017 | Wu .................. A61H 15/0078 |
| 2017/0304144 A1 | 10/2017 | Tucker |
| 2017/0304145 A1 | 10/2017 | Pepe |
| 2017/0312161 A1 | 11/2017 | Johnson et al. |
| 2017/0360641 A1* | 12/2017 | Nakata .................. A61H 7/007 |
| 2018/0008512 A1 | 1/2018 | Goldstein |
| 2018/0050440 A1 | 2/2018 | Chen |
| 2018/0078449 A1 | 3/2018 | Callow |
| 2018/0133101 A1 | 5/2018 | Inada |
| 2018/0140100 A1* | 5/2018 | Cribbs .................. A47C 7/14 |
| 2018/0140502 A1 | 5/2018 | Shahoian et al. |
| 2018/0141188 A1 | 5/2018 | Lai |
| 2018/0154141 A1 | 6/2018 | Ahn |
| 2018/0185234 A1* | 7/2018 | Ishiguro .............. A61H 23/0254 |
| 2018/0200141 A1 | 7/2018 | Wersland et al. |
| 2018/0236572 A1 | 8/2018 | Ukai |
| 2018/0243158 A1 | 8/2018 | Loghmani et al. |
| 2018/0263845 A1 | 9/2018 | Wersland et al. |
| 2018/0279843 A1 | 10/2018 | Paul et al. |
| 2018/0288160 A1 | 10/2018 | Paul et al. |
| 2018/0296433 A1 | 10/2018 | Danby et al. |
| 2018/0315499 A1 | 11/2018 | Appelbaum et al. |
| 2018/0315504 A1 | 11/2018 | Inada et al. |
| 2019/0000709 A1* | 1/2019 | Sone .................. A61H 23/0254 |
| 2019/0038229 A1 | 2/2019 | Perraut et al. |
| 2019/0066833 A1 | 2/2019 | Wicki |
| 2019/0110945 A1* | 4/2019 | Kawagoe .............. A61B 5/0057 |
| 2019/0175434 A1 | 6/2019 | Zhang |
| 2019/0209424 A1 | 7/2019 | Wersland et al. |
| 2019/0216677 A1 | 7/2019 | Paul |
| 2019/0232478 A1 | 8/2019 | Zawisza et al. |
| 2019/0254921 A1 | 8/2019 | Marton et al. |
| 2019/0254922 A1 | 8/2019 | Marton et al. |
| 2019/0314239 A1 | 10/2019 | Ci |
| 2019/0337140 A1 | 11/2019 | Shanklin |
| 2019/0350793 A1 | 11/2019 | Wersland et al. |
| 2019/0381271 A1 | 12/2019 | Jo |
| 2020/0000237 A1* | 1/2020 | Wu .................. A47C 7/407 |
| 2020/0009010 A1 | 1/2020 | Park et al. |
| 2020/0016027 A1 | 1/2020 | Kim et al. |
| 2020/0035237 A1* | 1/2020 | Kim .................. G06V 40/161 |
| 2020/0069510 A1 | 3/2020 | Wersland et al. |
| 2020/0085675 A1 | 3/2020 | Lee et al. |
| 2020/0090175 A1 | 3/2020 | Davis et al. |
| 2020/0179210 A1 | 6/2020 | Barragan Gomez |
| 2020/0179215 A1 | 6/2020 | Lerner |
| 2020/0230012 A1 | 7/2020 | Fuhr |
| 2020/0241683 A1 | 7/2020 | Le et al. |
| 2020/0261306 A1 | 8/2020 | Pepe |
| 2020/0261307 A1 | 8/2020 | Wersland et al. |
| 2020/0268594 A1 | 8/2020 | Pepe |
| 2020/0294423 A1 | 9/2020 | Blain et al. |
| 2020/0352821 A1 | 11/2020 | Wersland et al. |
| 2020/0390644 A1 | 12/2020 | Yang |
| 2020/0397651 A1 | 12/2020 | Park et al. |
| 2020/0405570 A1* | 12/2020 | Kodama .............. A61H 9/0078 |
| 2021/0000683 A1 | 1/2021 | Cheng |
| 2021/0022951 A1 | 1/2021 | Hu |
| 2021/0022955 A1 | 1/2021 | Wersland et al. |
| 2021/0059898 A1 | 3/2021 | Wersland et al. |
| 2021/0085555 A1 | 3/2021 | Davis et al. |
| 2021/0128402 A1 | 5/2021 | Dai et al. |
| 2021/0330539 A1 | 10/2021 | Faussett |
| 2022/0000706 A1* | 1/2022 | Grbic .................. A61H 15/00 |
| 2022/0000781 A9 | 1/2022 | Leneweit et al. |
| 2022/0007810 A1 | 1/2022 | Paspatis et al. |
| 2022/0054350 A1 | 2/2022 | Merino et al. |
| 2022/0087433 A1* | 3/2022 | Mao .................. F21S 4/28 |
| 2022/0241135 A1* | 8/2022 | Wang .................. A61H 23/006 |

FOREIGN PATENT DOCUMENTS

| | | | |
|---|---|---|---|
| CN | 86101310 A | | 9/1986 |
| CN | 1432452 A | | 7/2003 |
| CN | 2788807 Y | | 6/2006 |
| CN | 201239336 Y | | 5/2009 |
| CN | 201239338 Y | | 5/2009 |
| CN | 201333160 Y | | 10/2009 |
| CN | 201524220 U | | 7/2010 |
| CN | 101888050 A | | 11/2010 |
| CN | 201743890 U | | 2/2011 |
| CN | 201847899 U | | 6/2011 |
| CN | 301664182 S | | 9/2011 |
| CN | 202161539 U | | 3/2012 |
| CN | 202637439 U | | 1/2013 |
| CN | 103648320 A | | 3/2014 |
| CN | 203598194 U | | 5/2014 |
| CN | 104352341 A | | 2/2015 |
| CN | 303250924 S | | 6/2015 |
| CN | 303250929 S | | 6/2015 |
| CN | 205163583 U | | 4/2016 |
| CN | 104352341 B | | 7/2016 |
| CN | 205459750 U | | 8/2016 |
| CN | 205494357 U | | 8/2016 |
| CN | 205598186 U | | 9/2016 |
| CN | 106074129 A | * | 11/2016 |
| CN | 106236528 A | | 12/2016 |
| CN | 206081000 U | | 4/2017 |
| CN | 106859949 A | | 6/2017 |
| CN | 107374898 A | * | 11/2017 .............. A61H 1/00 |
| CN | 304561844 S | | 3/2018 |
| CN | 207286298 U | | 5/2018 |
| CN | 207855923 U | | 9/2018 |
| CN | 109259995 A | | 1/2019 |
| CN | 208405314 U | | 1/2019 |
| CN | 208448086 U | | 2/2019 |
| CN | 109528473 A | | 3/2019 |
| CN | 209154392 U | | 7/2019 |
| CN | 110868983 A | | 3/2020 |
| CN | 106618998 B | | 8/2020 |
| CN | 111616938 A | * | 9/2020 ......... A61H 15/0078 |
| CN | 111973419 A | * | 11/2020 |

(56) References Cited

FOREIGN PATENT DOCUMENTS

| | | | |
|---|---|---|---|
| CN | 113143721 A | 7/2021 | |
| CN | 113509366 A | 10/2021 | |
| CN | 113509369 A * | 10/2021 | |
| DE | 3633888 A1 | 4/1988 | |
| DE | 19905199 A1 | 7/2000 | |
| DE | 102015102112 A1 | 8/2015 | |
| DE | 202015005257 U1 | 10/2016 | |
| EP | 0436719 B1 | 5/1994 | |
| EP | 1728494 A1 | 12/2006 | |
| EP | 2080500 A1 | 7/2009 | |
| EP | 2328255 A1 | 6/2011 | |
| EP | 1728494 B1 | 1/2013 | |
| GB | 2066081 A | 7/1981 | |
| GB | 2262236 A | 6/1993 | |
| JP | S5230553 A | 3/1977 | |
| JP | S5428491 A | 3/1979 | |
| JP | H0219157 A | 1/1990 | |
| JP | H03218763 A | 9/1991 | |
| JP | H048128 B2 | 2/1992 | |
| JP | H0447440 A | 2/1992 | |
| JP | H0447440 U | 4/1992 | |
| JP | H0751393 A | 2/1995 | |
| JP | 2000189525 A | 7/2000 | |
| JP | 3077837 U | 6/2001 | |
| JP | 2002282322 A | 10/2002 | |
| JP | 2003077837 A | 3/2003 | |
| JP | 2005204777 A | 8/2005 | |
| JP | 2006034941 A | 2/2006 | |
| JP | 2006212228 A | 8/2006 | |
| JP | 2008510588 A | 4/2008 | |
| JP | 2008289616 A | 12/2008 | |
| JP | 2010534110 A | 11/2010 | |
| JP | 2011502369 A | 1/2011 | |
| JP | 5129032 B2 | 1/2013 | |
| JP | 2013119018 A | 6/2013 | |
| JP | 2014511240 A | 5/2014 | |
| JP | 2015035844 A | 2/2015 | |
| JP | 2015104422 A | 6/2015 | |
| JP | 2018518347 A | 7/2018 | |
| KR | 200313149 Y1 | 5/2003 | |
| KR | 200435552 Y1 | 1/2007 | |
| KR | 100752432 B1 | 8/2007 | |
| KR | 20090119424 A | 11/2009 | |
| KR | 101123926 B1 | 4/2012 | |
| KR | 101162978 B1 | 7/2012 | |
| KR | 101406275 B1 | 6/2014 | |
| KR | 20170106550 A | 9/2017 | |
| KR | 20170108550 A | 9/2017 | |
| KR | 20180031683 A | 3/2018 | |
| KR | 20200051098 A | 5/2020 | |
| RU | 2170567 C1 | 7/2001 | |
| TW | I359657 B | 3/2012 | |
| TW | 201440753 A | 11/2014 | |
| WO | WO-0119316 A2 | 3/2001 | |
| WO | WO-2009014727 A1 | 1/2009 | |
| WO | WO-2009102279 A1 | 8/2009 | |
| WO | WO-2011159317 A1 | 12/2011 | |
| WO | WO-2013114084 A1 | 8/2013 | |
| WO | WO-2013145346 A1 * | 10/2013 | A47C 7/402 |
| WO | WO-2014118596 A1 | 8/2014 | |
| WO | WO-2015038005 A2 | 3/2015 | |
| WO | WO-2018012105 A1 | 1/2018 | |
| WO | WO-2019186225 A1 * | 10/2019 | A61H 15/0078 |
| WO | WO-2021050861 A1 | 3/2021 | |

OTHER PUBLICATIONS

Machine translation of written description and claims for CN111616938 (Year: 2020).*

Machine translation of written description and claims for WO2013145346A1 (Year: 2013).*

Machine translation from Espacenet of written description and claims for CN106074129A (Year: 2016).*

Machine translation from Espacenet of written description and claims for CN111616938A (Year: 2020).*

Machine translation from Espacenet of written description and claims for CN111973419A (Year: 2020).*

Machine translation of description and claims via espacenet for CN113509369 (Year: 2021).*

Machine translation of description and claims via espacenet for CN107374898 (Year: 2017).*

International Search Report and Written Opinion of the International Searching Authority issued in International Application No. PCT/US2022/076238, filed Sep. 9, 2022, 11 pages.

Amazon: "OIVO Xbox One Controller Charger Dual Charging Station Updated Strap, Remote Charger Dock-2 Rechargeable Battery Packs Included," OIVO, Sep. 6, 2018, Especially annotated figures, Retrieved from Entire Document, 11 Pages.

Amazon: "PowerA Joy Con & Pro Controller Charging Dock Nintendo Switch," PowerA, Oct. 31, 2017, Especially annotated figures, Retrieved from Entire Document, 10 Pages.

Amazon: "Theragun G3PRO Percussive Therapy Device, White, Handheld Deep Muscle, Treatment Massager & Muscle Stimulator for Pain Relief, Recovery, Enhance Performance & Energize The Body," Feb. 13, 2019, Shown on pp. 1, 2 Pages, Retrieved from URL: https://www.amazon.com/dp/B07MJ2MCT3/ref=nav_timeline_asin?_encoding=UTF8&psc=1.

Anthony Katz, "The RAPTOR: Helps Patients and Saves Your Most Valuable Tool . . . Your Hands," DC Aligned:MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.

Bardwell D., "Wahl's Massage Products—Meant for Life's Big Pains," DougBardwell.com, Apr. 6, 2016, 7 Pages, [Retrieved On Jun. 3, 2021] Retrieved from URL: https://dougbardwell.com/db/2016/04/06/wahls-massage-products-meant-for-lifes-big-pains/.

Collins D., "External Rotor Motor Basics: Design and Applications," Jun. 6, 2018, 03 Pages.

Collins D., "FAQ: What are Hall Effect Sensors and What Is Theirs Role In Dc Motors?," Jan. 11, 2017, 03 Pages.

Defendant's Initial Invalidity Contentions, *Therabody, Inc.* v. *Tzumi Electronics LLC et al.*, Case No. SDNY-1-21-cv-07803 (PGG)(RWL), dated Aug. 17, 2022; 16 pages.

Description of Therabody GI Device, available at: https://www.therabody.com/us/en-us/faq/thearagun-devices/faq-devices-1.html?fdid=faq&csortb1=sortOrder&csortd1=1 (last visited Feb. 15, 2023).

Digi-Key's North American Editors: "How to Power and Control Brushless DC Motors," Dec. 7, 2016, 09 Pages.

Examination Report For Australian Patent Application No. 2016284030, dated May 7, 2018, 3 Pages.

Extended European Search Report for European Application No. 16815104.1, dated Jan. 23, 2019, 08 Pages.

Extended European Search Report for European Application No. 18832213.5, dated Jul. 21, 2021, 11 Pages.

Extended European Search Report for European Application No. 18832923.9, dated Apr. 23, 2021, 7 Pages.

Extended European Search Report for European Application No. 20720323.3, dated Sep. 9, 2021, 10 Pages.

Extended European Search Report for European Application No. 20802710.2, dated May 10, 2022, 9 Pages.

Extended European Search Report for European Application No. 20802804.3, dated Apr. 28, 2022, 8 Pages.

Extended European Search Report for European Application No. 21178300.6, dated Oct. 19, 2021, 9 Pages.

Extended European Search Report for European Application No. 21178311.3, dated Sep. 23, 2021, 5 Pages.

Holly Riddle, "Theragun vs. Hyperice vs, Hydragun: Massage Gun Showdown [Buyer's Guide]," ChatterSource: Health & Wellness, Mar. 9, 2021, available at: https://www.chattersource.com/article/massage-gun/ (last visited Feb. 17, 2023); 14 pages.

International Preliminary Report on Patentability for International Application No. PCT/US2016/038326, dated Jan. 4, 2018, 8 Pages.

International Preliminary Report on Patentability for International Application No. PCT/US2018/022426, dated Sep. 26, 2019, 9 Pages.

(56) References Cited

OTHER PUBLICATIONS

International Preliminary Report on Patentability for International Application No. PCT/US2018/039599, dated Jan. 23, 2020, 8 Pages.
International Preliminary Report on Patentability for International Application No. PCT/US2018/040795, dated Jan. 23, 2020, 7 Pages.
International Preliminary Report on Patentability for International Application No. PCT/US2019/067624, dated Jul. 8, 2021, 11 Pages.
International Preliminary Report on Patentability for International Application No. PCT/US2020/017645, dated Aug. 26, 2021, 11 Pages.
International Preliminary Report on Patentability for International Application No. PCT/US2020/031339, dated Nov. 18, 2021, 11 Pages.
International Preliminary Report on Patentability for International Application No. PCT/US2020/031936, dated Nov. 18, 2021, 14 Pages.
International Preliminary Report on Patentability for International Application No. PCT/US2020/050385, dated Mar. 24, 2022, 12 Pages.
International Preliminary Report on Patentability for International Application No. PCT/US2020/050399, dated Jan. 13, 2022, 6 Pages.
International Preliminary Report on Patentability for International Application No. PCT/US2020/054773, dated Apr. 21, 2022, 8 Pages.
International Preliminary Report on Patentability for International Application No. PCT/US2020/054842, dated Apr. 21, 2022, 7 Pages.
International Preliminary Report on Patentability for International Application No. PCT/US2020/063426, dated Jun. 16, 2022, 06 Pages.
International Preliminary Report on Patentability for International Application No. PCT/US2021/022500, dated Oct. 6, 2022, 6 Pages.
International Preliminary Report on Patentability for International Application No. PCT/US2021/029900, dated Nov. 10, 2022, 9 Pages.
International Preliminary Report on Patentability for International Application No. PCT/US2021/029903, dated Nov. 10, 2022, 7 Pages.
International Search Report and Written Opinion for International Application No. PCT/US2016/038326, dated Sep. 1, 2016, 9 Pages.
International Search Report and Written Opinion for International Application No. PCT/US2018/022426, dated May 31, 2018, 10 Pages.
International Search Report and Written Opinion for International Application No. PCT/US2018/039599, dated Sep. 24, 2018, 9 Pages.
International Search Report and Written Opinion for International Application No. PCT/US2018/040795, dated Sep. 24, 2018, 8 Pages.
International Search Report and Written Opinion for International Application No. PCT/US2019/067624, dated Feb. 3, 2020, 13 Pages.
International Search Report and Written Opinion for International Application No. PCT/US2020/017645, dated May 20, 2020, 13 Pages.
International Search Report and Written Opinion for International Application No. PCT/US2020/031339, dated Jun. 10, 2020, 12 Pages.
International Search Report and Written Opinion for International Application No. PCT/US2020/031347, dated Aug. 3, 2020, 9 Pages.
International Search Report and Written Opinion for International Application No. PCT/US2020/031936, dated Sep. 11, 2020, 17 Pages.
International Search Report and Written Opinion for International Application No. PCT/US2020/050385, dated Dec. 3, 2020, 13 Pages.
International Search Report and Written Opinion for International Application No. PCT/US2020/050399, dated Feb. 4, 2021, 11 Pages.
International Search Report and Written Opinion for International Application No. PCT/US2020/054773, dated Jan. 12, 2021, 9 Pages.
International Search Report and Written Opinion for International Application No. PCT/US2020/054842, dated Jan. 11, 2021, 8 Pages.
International Search Report and Written Opinion for International Application No. PCT/US2020/063426, dated Feb. 26, 2021, 09 Pages.
International Search Report and Written Opinion for International Application No. PCT/US2021/022500, dated Apr. 20, 2021, 7 Pages.
International Search Report and Written Opinion for International Application No. PCT/US2021/029900, dated Oct. 6, 2021, 12 Pages.
International Search Report and Written Opinion for International Application No. PCT/US2021/029903, dated Jul. 28, 2021, 8 Pages.
International Search Report and Written Opinion for International Application No. PCT/US2022/028309, dated Sep. 8, 2022, 10 Pages.
Massage Expert: "Nursal Deep Percussion Massager Review—6 Interchangeable Nodes," Jan. 4, 2021, 6 Pages, [Retrieved on Jun. 3, 2021] Retrieved from URL: https://www.massageexpert.net/nursal-deep-percussion-massager-review/.
McFarland M., "Segway Was Supposed to Change the World, Two Decades Later, It Just Might," CNN Wire Service, Oct. 30, 2018, 7 Pages.
Notice of Reasons for Rejection for Japanese Patent Application No. 2018-517683, dated Oct. 2, 2018, 10 Pages.
Office Action For Canadian Application No. 2,990,178, dated Oct. 15, 2018, 4 Pages.
Partial Supplementary European Search Report for European Application No. 18832213.5, dated Apr. 20, 2021, 12 Pages.
Rachel [no family name indicated], "Jigsaw Massager," Instructables, Apr. 18, 2010, 6 Pages, Retrieved from URL: https://web.archive.org/web/20100418041422/http://www.instructables.com/id/Jigsaw-Massager/.
Rockwell: "Trans4mer Operating Manual for Multi-purpose saw," Model RK2516/RK2516K, 2011, 32 Pages.
Supplementary European Search Report for European Application No. 19904459.5, dated Apr. 15, 2021, 04 Pages.
Testberichte.de: "Naipo Handheld Percussion Massager with Heating (MGPC 5000)," amazon.de, 7 Pages, [Retrieved on 2021-06-03] Retrieved from URL: https://www.testberichte.de/p/naipo-tests/handheld-percussion-massager-with-heating-mgpc-5000-testbericht.html, See also a YouTube Review of this Device dated May 21, 2018 at https://www.youtube.com/watch?v=bi_QCJA3D9k.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Visual Description of Hyper Ice, Inc. Raptor Device, "Raptor Solutions 1.3 Prone," available at: https://www.youtube.com/watch?v=6i1tRqdwPU8&t=156s (last visited Feb. 15, 2023); 1 page.
WORX: "Safety and Operating Manual Original Instructions," for 12V Li-lon Multipurpose saw, WX540, WX540.3, WX540.9, Trans4mer, 2013, 16 Pages.
WORX Trans4mer "Safety and Operating Manual Original Instructions" for 12V Li-lon Multipurpose saw, WX540, NX540.3, WX540.9, 16 pages (2013).
YouTube: "Unboxing: Joy-Con & Pro Controller Charging Dock for Nintendo Switch," Crusherbad64, Especially demonstration 8:30 - 8:55, (This reference is Being Used to Show Greater Details of Product not Clearly Disclosed in 'PowerA'), Feb. 26, 2018, Retrieved from entire document, 1 Page.

\* cited by examiner

CHAIR INCLUDING PERCUSSIVE MASSAGE THERAPY

CROSS-REFERENCE TO RELATED APPLICATION

This application claims the benefit of U.S. Provisional Application No. 63/242,621, filed on Sep. 10, 2021, the entirety of which is incorporated herein by reference.

BACKGROUND

In some applications, furniture with integrated massaging features can provide a desirable alternative to handheld massage tools. For example, some users may find it easier to relax or meditate when sitting or reclining on massaging furniture than when actively applying a tool. However, such massage furniture is typically constructed with unremovable massage features at fixed locations. Existing massage furniture therefore tends to provide limited options for how and where treatment can be applied.

SUMMARY

Described herein is a chair that includes a plurality of therapeutic features, including percussive massage or percussive therapy, pneumatic compression of the legs and/or arms, far infrared (FIR) technology and sound therapy, among others. Massage chairs allow users to sit and receive a back and/or leg kneading type massage via various mechanisms.

Percussive massage is a type of massage wherein a massage head of a tool, sometimes located at the distal end of a shaft that reciprocates along a proximal distal axis, repeatedly contacts the user. The chair of the present disclosure includes one or more percussive massage assemblies on a carriage that may travel along a cavity of the chair to target specific portions of the user. The attachment or massage head of the percussive massage assemblies may be configured to reciprocate at a frequency of between about 15 Hz and about 100 Hz, and at an amplitude of between about 0.15 and about 1.0 inches, though a wide range of other frequencies and amplitudes are suitable for use with the concepts of the present disclosure. In some embodiments, the output shaft is configured to reciprocate the attachment (whether removable or not) at a frequency of between about 25 Hz and about 48 Hz, and at an amplitude of between about 0.23 and about 0.70 inches. In some embodiments, the output shaft is configured to reciprocate the attachment at a frequency of between about 33 Hz and about 42 Hz, and at an amplitude of between about 0.35 and about 0.65 inches (all measurements can be in inches or millimeters e.g., 16 mm). Amplitude and/or frequency can be adjustable. Kneading massage is the type of massage that is provided by massage chairs, where a roller or the like pushes into and moves against the person's back or other body part.

In some aspects, a massage chair may comprise a seat portion, a back portion, a leg portion, and a massage carriage configured to move within the seat portion, the back portion, and the leg portion. The massage carriage may comprise a percussive massage assembly comprising a motor, a reciprocating shaft coupled to the motor and configured to reciprocate in response to activation of the motor, and a reciprocating massage head coupled to the reciprocating shaft. The massage chair may also comprise a support mechanism associated with the percussive massage assembly. The support mechanism may be configured to support a weight of a user of the massage chair, thereby allowing the reciprocating shaft and the reciprocating massage head of the percussive massage assembly to reciprocate.

In some arrangements according to any of the foregoing, the reciprocating massage head may be configured to reciprocate at a frequency between about 15 Hz and about 100 Hz and at an amplitude of between about 3 mm and about 25 mm.

In some arrangements according to any of the foregoing, the leg portion may include at least a first leg pneumatic compression assembly.

In some arrangements according to any of the foregoing, the first leg pneumatic compression assembly may be removable from the leg portion.

In some arrangements according to any of the foregoing, the massage chair may further comprise first and second arm portions, wherein the first arm portion includes a first arm pneumatic compression assembly, and wherein the second arm portion includes a second arm pneumatic compression assembly.

In some arrangements according to any of the foregoing, the first and second pneumatic compression assemblies may be removable from the first and second arm portions.

In some arrangements according to any of the foregoing, the massage chair may further comprise one or more far infrared (FIR) elements configured to provide FIR therapy to the user of the massage chair.

In some arrangements according to any of the foregoing, the one or more FIR elements may comprise at least one of a far infrared fabric and far infrared light emitters.

In some arrangements according to any of the foregoing, the massage chair may comprise one or more speakers configured to provide haptic sound therapy to the user of the massage chair.

In some arrangements according to any of the foregoing, the percussive massage assembly may be mounted on the massage carriage, and the massage carriage may comprise a kneading massage assembly.

In some arrangements according to any of the foregoing, one or more movements and operations of components in the massage carriage may be controlled by a controller coupled to the massage chair.

In some arrangements according to any of the foregoing, the controller coupled to the massage chair may be operated by the user of the massage chair by providing user input via an application installed on a user device of the user.

In some arrangements according to any of the foregoing, the massage chair may comprise one or more dampeners arranged between portions of the massage carriage and the percussive massage assembly, wherein the one or more dampeners are configured to dampen one or more vibrations generated by the motor of the percussive massage assembly.

In some arrangements according to any of the foregoing, the massage chair may comprise a frame underneath the seat, the leg, and the back portions. The massage chair may also comprise one or more tracks coupled to the frame, wherein the massage carriage is configured to move along the one or more tracks.

In some arrangements according to any of the foregoing, one or more dampeners may be arranged between the one or more tracks and the frame, wherein the one or more dampeners are configured to dampen one or more vibrations generated by movement of the massage carriage along the one or more tracks.

In some arrangements according to any of the foregoing, the massage chair may comprise a central cavity below the seat, the leg, and the back portions. The central cavity may be configured to house the frame, the one or more tracks, and the massage carriage.

In some arrangements according to any of the foregoing, the massage chair may comprise a cover arranged over the central cavity. The massage chair may also comprise a support strap. The cover may be coupled to the massage chair by the support strap.

In some arrangements according to any of the foregoing, a first end of the support strap may be attached to an interior surface of the cover, and a second end of the support strap may be attached to the back portion of the massage chair In another aspect, which may coexist with any of the foregoing concepts, a massage chair may comprise a percussive massage device, and the percussive massage device may comprise a housing that defines a housing interior, a thickness, a width and a height. The percussive massage device may also comprise a motor positioned in the housing, wherein the motor includes a rotatable motor shaft that defines a motor axis. The percussive massage device may also comprise a counterweight that rotates about the motor axis. The percussive massage device may also comprise a reciprocating shaft operatively connected to the motor and configured to reciprocate in response to activation of the motor, wherein the reciprocating shaft includes a distal end that defines a reciprocation axis, the reciprocation axis defines a thickness reciprocation plane that extends transversely through the thickness of the housing and divides the housing into first and second side portions, and the motor is positioned in the first side portion, and wherein the motor axis is perpendicular to the reciprocation axis.

In some arrangements according to any of the foregoing, the percussive massage device may comprise a battery located in the housing on an opposite side of the thickness reciprocation frame from the motor. The battery may power the motor.

In some arrangements according to any of the foregoing, the battery may extend along a battery axis that is perpendicular to the motor axis and parallel to the reciprocation axis.

In some arrangements according to any of the foregoing, the massage chair may comprise a carriage to which the percussive massage device is mounted, the carriage being movable within the massage chair.

In some arrangements according to any of the foregoing, the massage chair may comprise rails extending from a leg portion of the massage chair to a back portion of the massage chair and the carriage comprises wheels for travelling along rails.

In some arrangements according to any of the foregoing, the rails may comprise teeth and the carriage may comprise a motorized gear in a rack and pinion arrangement with the teeth.

In another aspect that may coexist with any of the foregoing concepts, a massage chair or other massage furniture may comprise a percussive massage device. The percussive massage device may comprise a housing that defines a housing interior, wherein the housing defines a thickness, a width and a height. The percussive massage device may also comprise a battery, a motor positioned in the housing, wherein the motor includes a rotatable motor shaft that defines a motor axis, a counterweight that rotates about the motor axis, and a switch for activating the motor. The percussive massage device may also comprise a reciprocating shaft operatively connected to the motor and configured to reciprocate in response to activation of the motor, wherein the reciprocating shaft includes a distal end that defines a reciprocation axis, wherein the reciprocation axis defines a thickness reciprocation plane that extends transversely through the thickness of the housing and divides the housing into first and second side portions, wherein the entire motor is positioned on a first side of the thickness reciprocation plane in the first side portion and the entire battery is positioned on a second side of the thickness reciprocation plane in the second side portion, wherein the motor axis extends perpendicular to the thickness reciprocation plane and extends through the battery, and wherein the first side portion is symmetrical to the second side portion except for any openings or ports defined in the housing.

In another aspect that may coexist with any of the foregoing concepts, a massage chair may comprise a percussive massage device. The percussive massage device may comprise a housing that defines a housing interior, a thickness, a width and a height. The percussive massage device may also comprise a battery that defines a battery axis, a motor positioned in the housing, wherein the motor includes a rotatable motor shaft that defines a motor axis. The percussive massage device may also comprise a counterweight that rotates about the motor axis and a switch for activating the motor. The percussive massage device may also comprise a reciprocating shaft operatively connected to the motor and configured to reciprocate in response to activation of the motor, wherein the reciprocating shaft includes a distal end that defines a reciprocation axis, wherein the reciprocation axis defines a thickness reciprocation plane that extends transversely through the thickness of the housing and divides the housing into first and second side portions, wherein the motor is positioned in the first side portion, and wherein the first side portion is symmetrical to the second side portion except for any openings or ports defined in the housing, wherein the battery axis is parallel to the reciprocation axis, and wherein the motor axis is perpendicular to the reciprocation axis and the battery axis.

DETAILED DESCRIPTION OF THE EMBODIMENTS

Figure 1A:
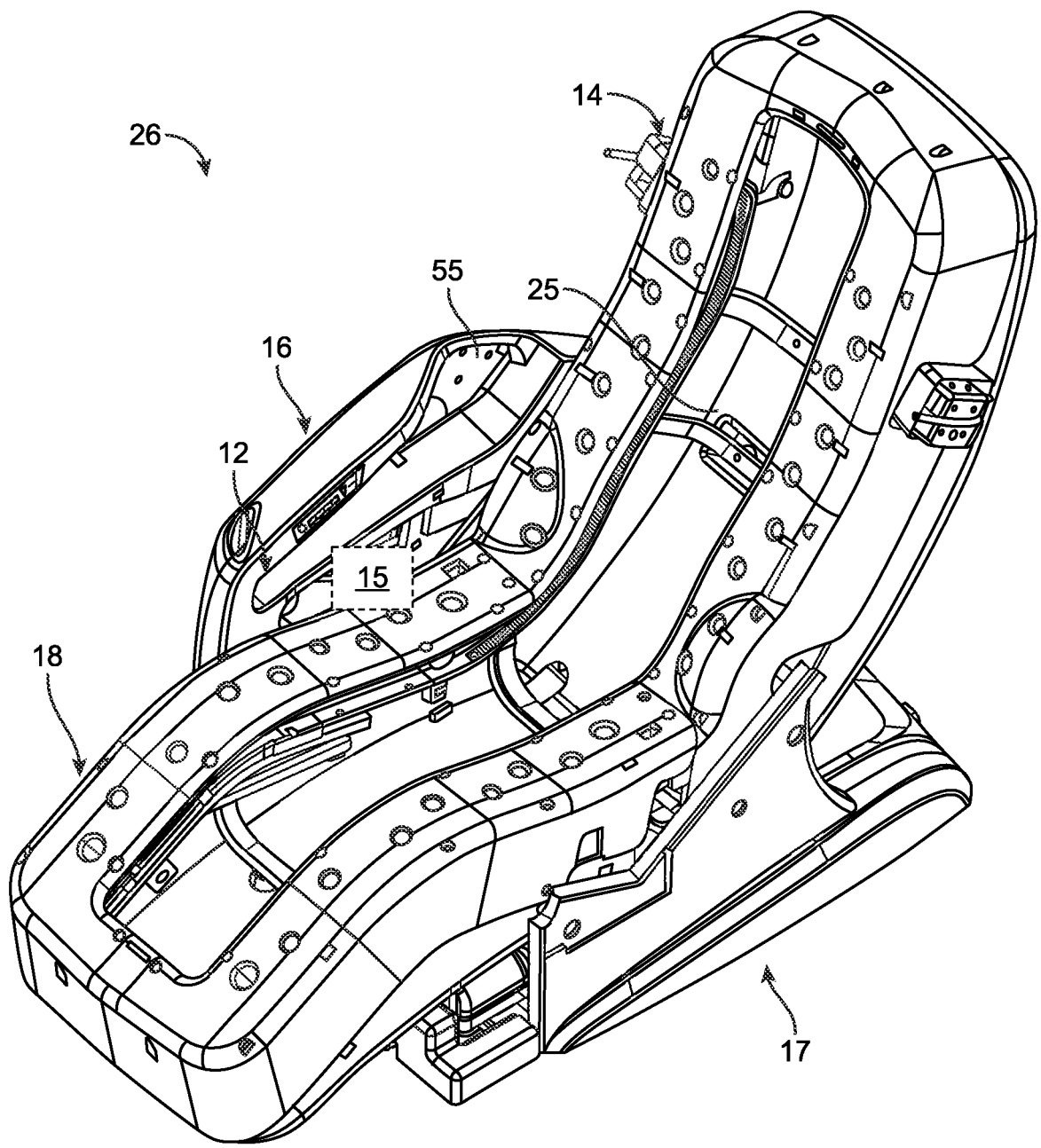
FIG. 1A is an upper perspective view of a frame of a chair according to the present disclosure.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the disclosure may be applied to another aspect or embodiment of the disclosure. Similarly, where appropriate any of the features discussed herein in relation to one aspect or embodiment of the disclosure may be optional with respect to and/or omitted from that aspect or embodiment of the disclosure or any other aspect or embodiment of the disclosure discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present disclosure.

FIG. 1 shows an exemplary therapeutic chair frame 26 that includes a seat portion 12, a back portion 14, two arm portions 16, though, for illustrative purposes, only one arm portion 16 is illustrated in FIG. 1A, and a leg portion 18. The frame 26 is a portion of a chair 10, which is shown in FIGS. 4A-4D and described further below, that remains when certain external cushions and fabric are removed. The seat portion 12, back portion 14, arm portions 16, and leg portion 18 of the chair frame 26 therefore correspond to a seat portion, a back portion, arm portions, and a leg portion of the chair 10, and such portions of the chair frame 26 and the chair 10 may be referred to interchangeably.

Figure 1B:
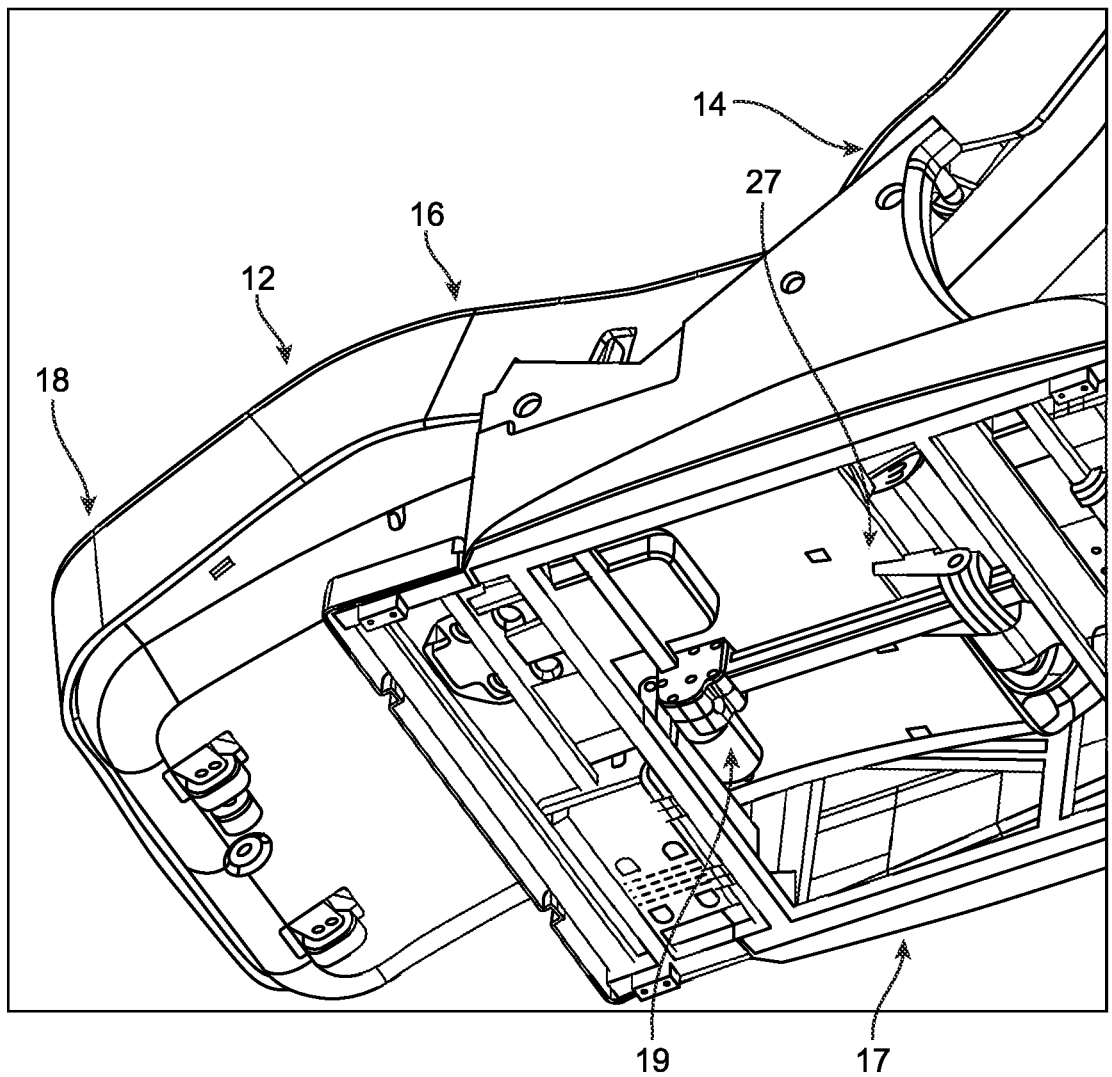
FIG. 1B is a lower perspective view of the frame of FIG. 1A.

The chair 10 is configured for a person to sit therein and receive therapeutic or recovery treatments to various body parts, such as their back, legs, arms, head, butt and feet, and the chair frame 26 includes mechanical features to support this functionality. For example, in some embodiments, the chair frame 26, and thus the chair 10, may be reclined or adjusted, such that the back portion 14, seat portion 12, and leg portion 18 of the chair 10 are reclined to a zero gravity position. In the illustrated example, as shown in FIG. 1B, the back portion 14 and seat portion 12 are rotatably mounted to a base 17. A linear actuator 19 is pivotably connected to the base 17 and a bracket 27 that is connected to the seat portion 12. The angular position of the back portion 14, seat portion 12, and leg portion 18 can therefore be adjusted by using the linear actuator 19 to force the bracket 27 nearer to or farther from the point where the linear actuator 19 connects to the base 17. However, in other examples, any other mechanism may be used to enable adjustment of the seat portion 12, back portion 14, and leg portion 18, either collectively or individually.

Figure 1C:
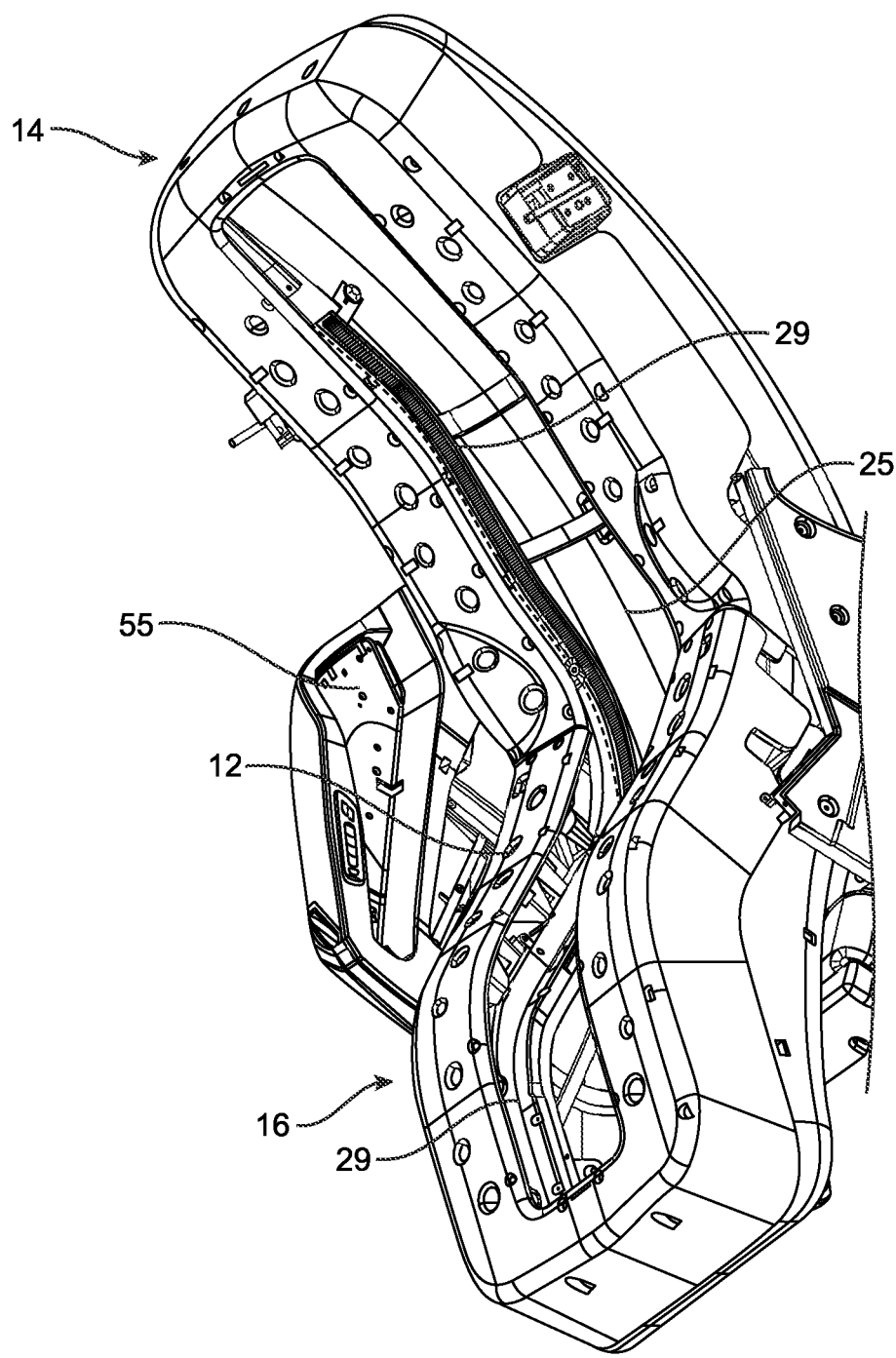
FIGS. 1C and 1D are side perspective views of the frame of FIG. 1A.
Figure 1D:
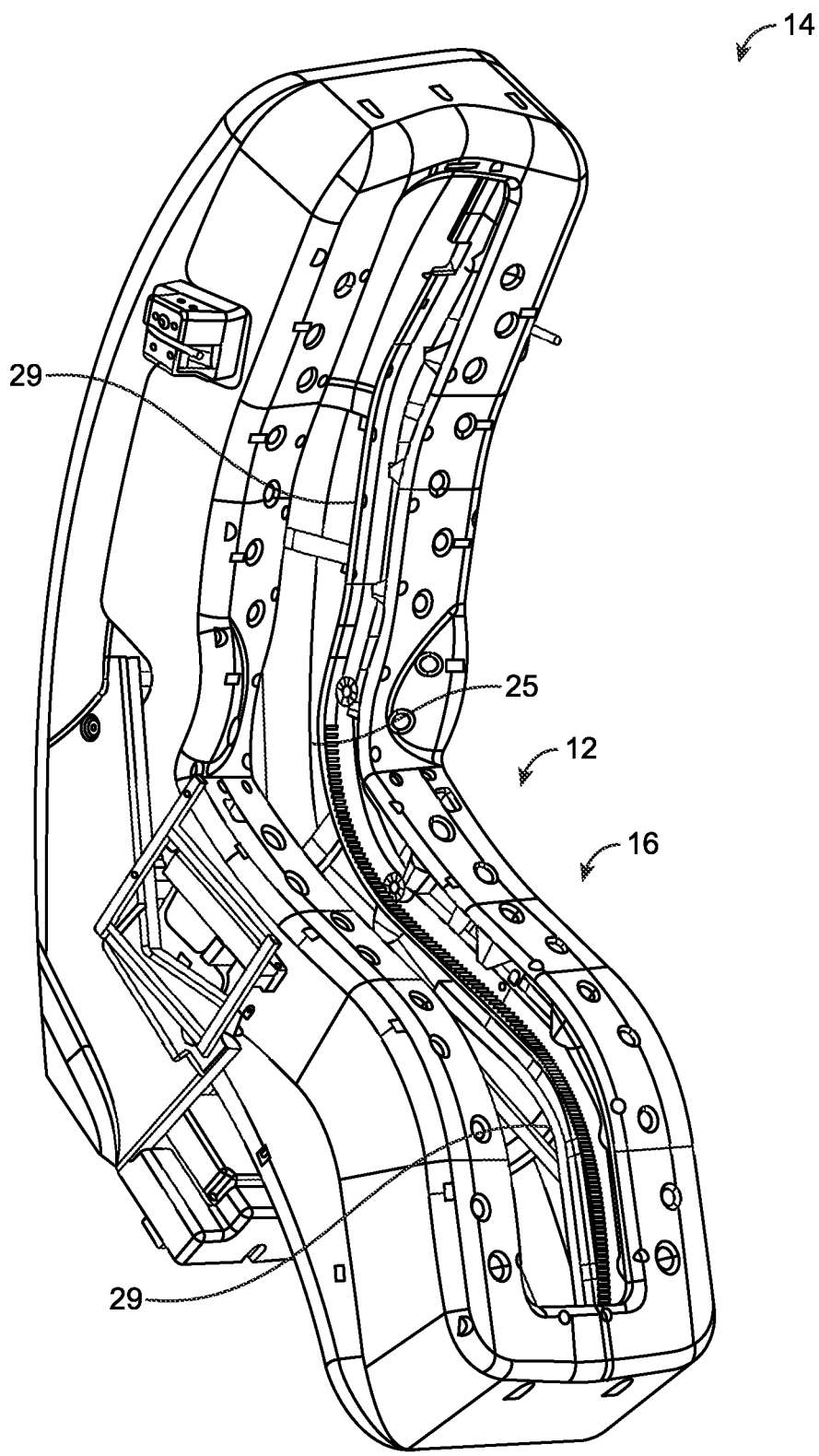

As shown in FIGS. 1A, 1C, and 1D, the seat portion 12, back portion 14, and leg portion 18 collectively define elongate central cavity 25. In the illustrated example, the cavity 25 extends continuously from an upper end of the back portion 14, across the seat portion 12, and to a lower end of the leg portion 18, thus enabling a single carriage 20, described below, to travel from where users would rest their heads to where users would rest their feet. Rails 29 extend along either side of the cavity 25 for the carriage 20 to travel along. However, in other examples, the chair frame 26 may instead define two or more discontinuous cavities with corresponding rails, and two or more carriages 20 may be disposed therein to independently treat different portions of a user. In further examples, two or more parallel cavities may exist at some or all points along the length of the chair frame 26 instead of the single cavity 25 shown in the illustrated example.

Figure 2A:
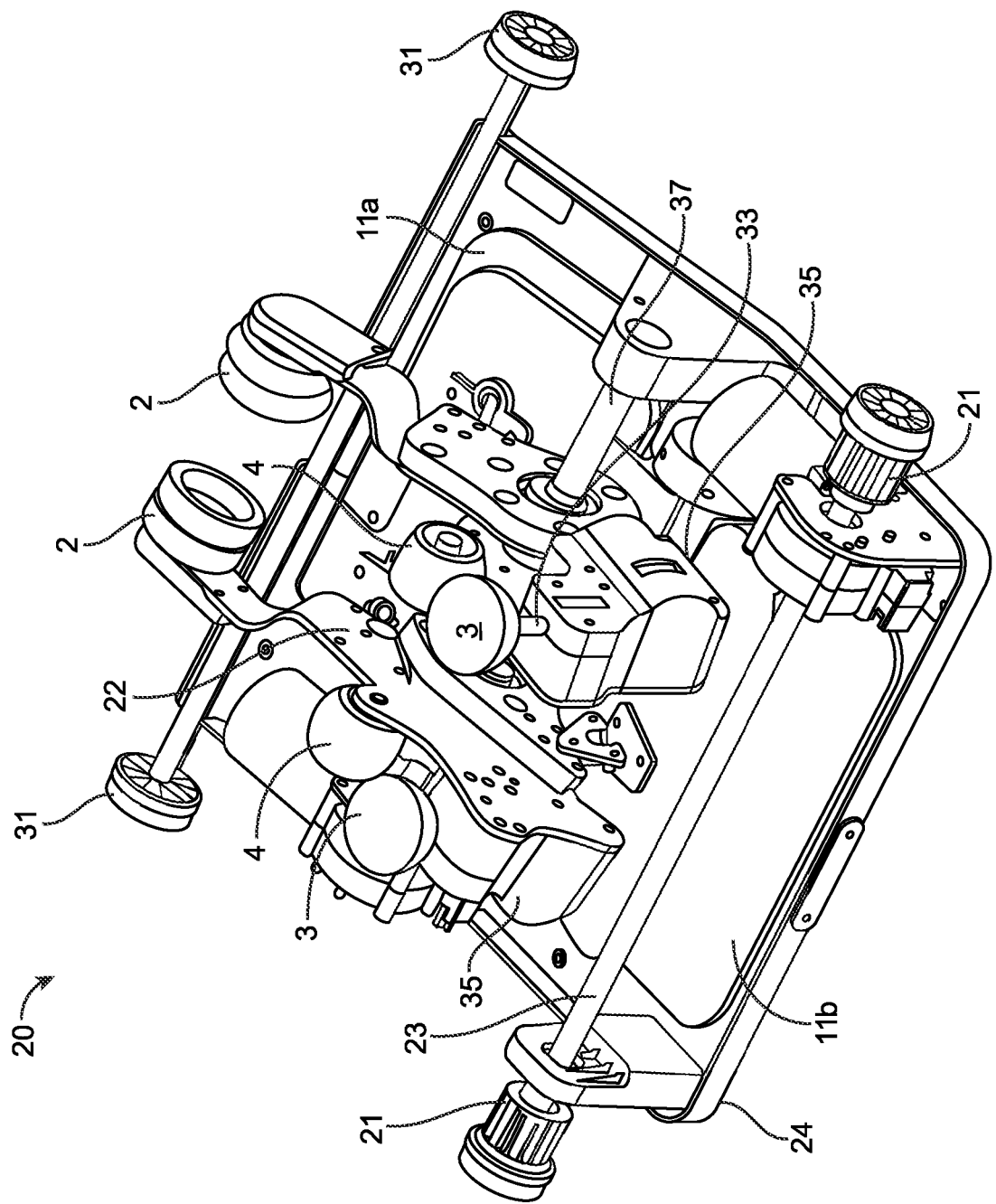
FIG. 2A is a front perspective view of a massage carriage for use with the frame of FIG. 1A.
Figure 2B:
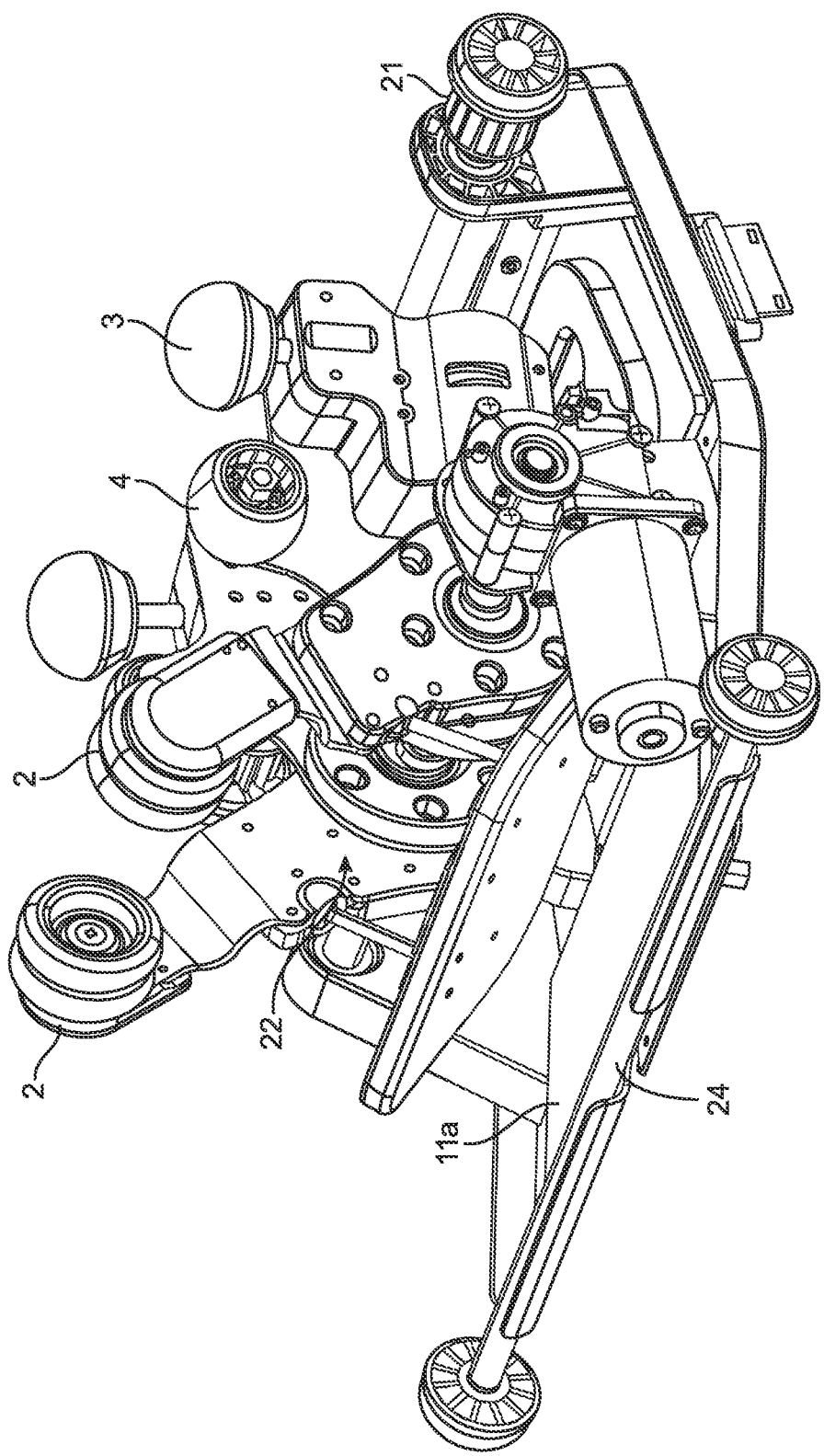
FIG. 2B is a back perspective view of the carriage of FIG. 2A.
Figure 2C:
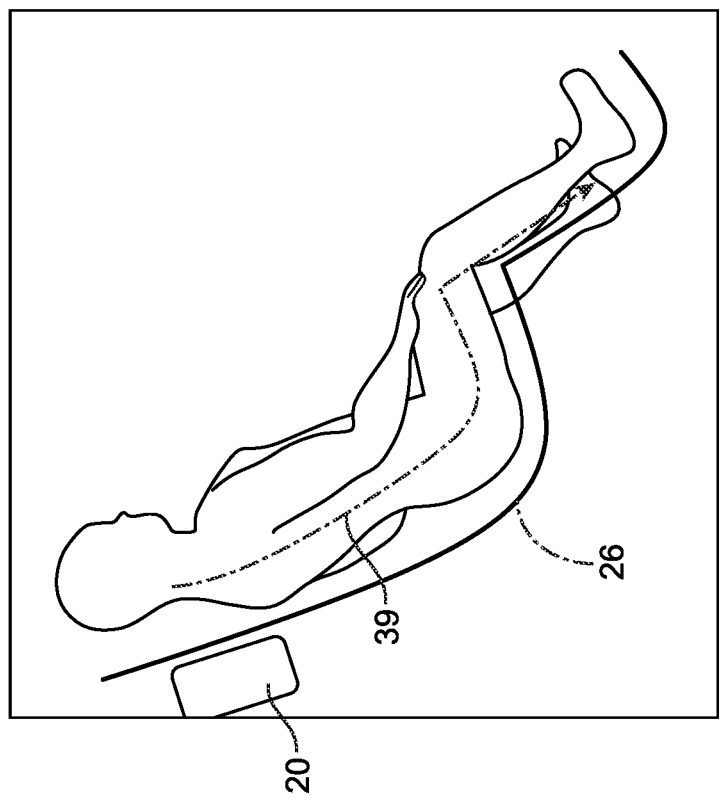
FIG. 2C is a diagrammatic illustration of a range of travel of the carriage of FIG. 2A.

FIGS. 2A and 2B illustrate a massage carriage 20 that may be included in the chair 10 and received in the cavity 25. The carriage 20 of the illustrated example includes percussive massage capability and/or kneading massage capability. In some embodiments, the massage carriage 20 may be referred to herein as a massage cart or module used to carry or hold the massage elements or components. The massage carriage 20 may be configured to move along the back portion 14, seat portion 12 and leg portions 18 so that massage can be provided to different body parts. For that purpose, the massage carriage 20 of the illustrated example includes gears 21 on a motorized axle 23. The gears 21 can engage teeth extending along the rails 29 to form rack and pinion arrangements on either side of the cavity 25 so that driving the axle 23 causes the carriage to travel along the rails 29. Because of the extent of the cavity 25, the massage carriage 20 can access a range 39 on a typical user's body that extends from the user's head to the user's feet. The massage carriage 20 can therefore move up and down in the illustrated arrangement, though in other arrangements the massage carriage 20 may be configured to move or longitudinally, side to side or laterally and in or out (toward or away from the seated user), or any combination thereof, instead of or in addition to the up and down movement of the illustrated example. The carriage 20 also includes wheels 31, which are spaced from the gears 21 and are configured to travel passively along the rails 29 as the gears 31 move the carriage 20. Thus, the wheels 31 cooperate with the gears 21 to cause the carriage 20 to rotate as it follows the curves of the tracks 29. The spatial relationship between the wheels 31 and the gears 21 is such that massage heads 2 and 3 and supports 4 will generally protrude from the cavity 25 and toward a space that would be occupied by the body of a user sitting in the chair. In other examples, the carriage 20 may include only one gear 21, and thus only form a single rack and pinion arrangement on one side of the cavity 25. Moreover, instead of the rack and pinion arrangements, the chair 10 according to other arrangements can include one or more tracks, rails, conveyors, chains or other components configured to move the massage carriage 20 on or along the chair frame 26 and/or configured to move a component or part thereof to the desired position and location or as a part of routines that can be controlled by a central controller 15 coupled to the massage chair. The controller 15 is illustrated as being housed in one of the arm portions 16, but the controller could be located anywhere in the chair. Moreover, for any reference to the controller herein 15, the functions there described could instead be executed by different, dedicated controller or a distributed system of controllers.

Figure 1E:
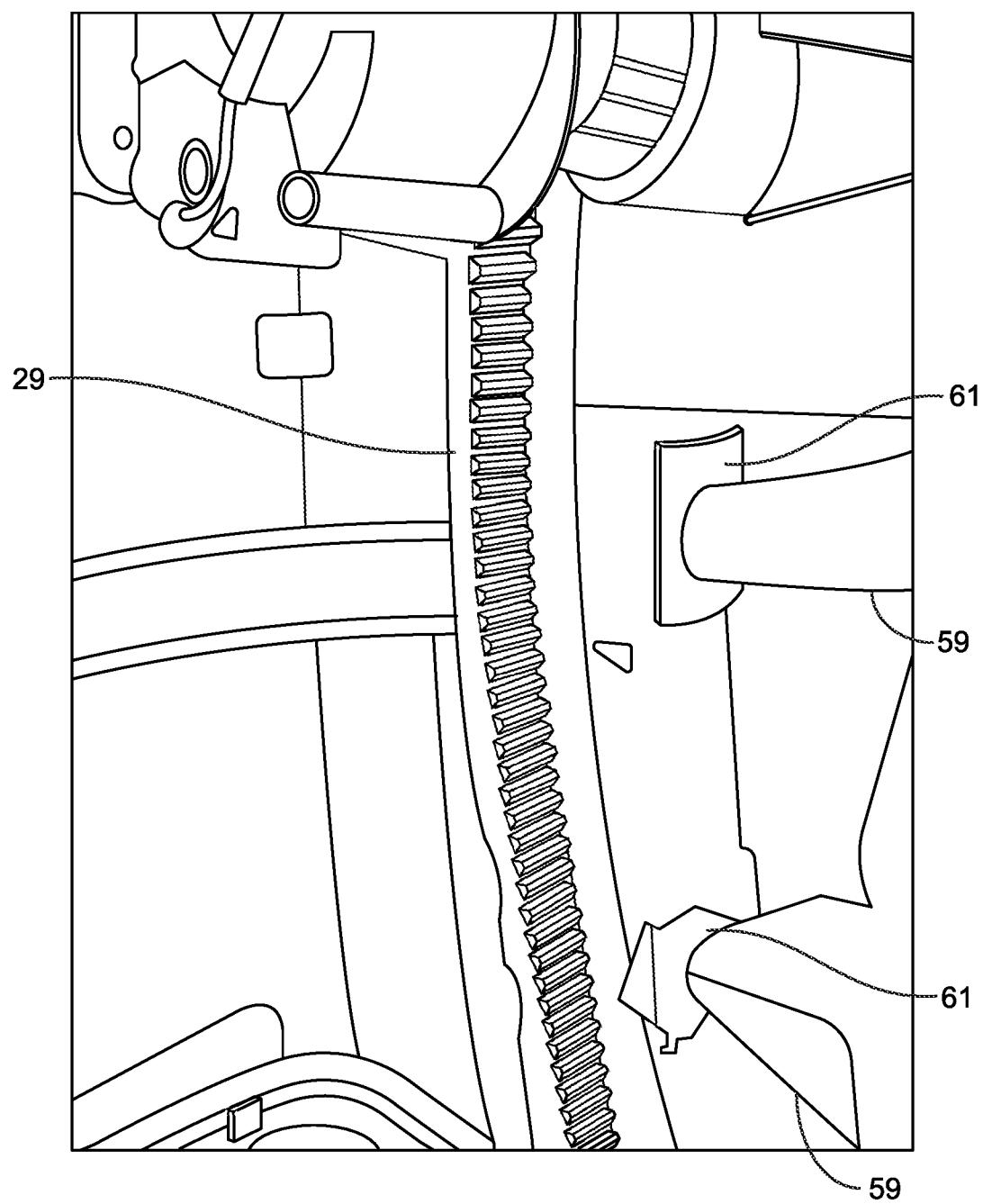
FIG. 1E is an enlarged view of a constructional detail of the frame of FIG. 1A.

FIG. 1E is a close view of a portion of one of the rails 29. The portion of the rail 29 shown in FIG. 1E has a series of parallel ribs or teeth, which may be engaged by gear teeth. In the illustrated example, the rails 29 are connected to the rest of the chair frame 26 by pillars 59 that are attached to a flange of each rail. A vibration damping pad 61, which may be made of any vibration damping material, such as, for example, foam, rubber, or silicone, is disposed between each pillar 59 and the flange of the rail 29. The pads 61 therefore reduce the amount of vibration transmitted from the rail 29 or anything supported by the rail 29 to the rest of the chair frame 26. The pillar 59 construction shown is merely one example of how the rails 29 may be attached to the rest of the chair frame 26, and the pads 61 may be applied in any other construction to reduce transmission of vibration. In other examples, the pads 61 may be omitted.

As shown in FIGS. 2A and 2B, the massage carriage 20 includes one or more kneading massage heads 2 (and accompanying components), one or more percussive massage heads 3 (and accompanying components), a carriage frame 22 for mounting the massage heads thereon, one or more airbags 11a and 11b and one or more support mechanisms or members 4. In some embodiments, one or more airbags 11 may include two airbags 11a and 11b that are configured to inflate and/or deflate based on detecting one or more force values through a force meter in the percussive massage head 3. In some embodiments, the airbag 11a may be associated with the kneading massage heads 2, and the airbag 11b may be associated with the percussive massage head 3. These components are mounted or arranged on a platform 24 or the like. The supports 4 of the illustrate examples are wheels or rollers and can therefore travel smoothly along the wearer's body even when load is applied. In some embodiments, the percussive massage heads 3 and accompanying components may be referred to herein as a percussive massage assembly. Each percussive massage assembly includes shaft 33 and a motor 35 configured to drive the shaft 33 to reciprocate along a respective proximal-distal axis. In each percussive massage assembly, the percussive massage head 3 is attached to the distal end of the shaft 33.

In the illustrated embodiment the carriage frame 22 includes multiple parts, each of which is independently pivotably connected to the platform 24 by a shaft 37 so the airbag(s) 11 provide movement or adjustment for the kneading massage heads 2 independently of the percussive massage heads 3 and supports 4. That is, one of the airbags 11 pushes the percussive massage heads 3 and supports 4 away from the platform 24 when inflated, while the other of the airbags 11 pushes the kneading massage heads 3 away from the platform 24. In some embodiments, the kneading massage heads 2 and the percussive massage heads 3 may comprise an adjustable height and an adjustable width. Inflating the airbag 11 moves one or more of the kneading massage heads 2 and/or percussive massage heads 3 away from the platform 24 and toward the user, thereby increasing the intensity of the massage. Deflating the airbag 1 decreases the intensity of the massage. The airbag 1 also helps absorb the vibrations to help prevent the entire chair from vibrating. By contrast, in other examples wherein the percussive massage mechanisms are connected rigidly to the chair 10, the whole chair 10 tends to vibrate when the percussive massage mechanisms are active. In some embodiments, the airbags 11 may be controlled by an overall system controller 15, shown in FIG. 1A, that is configured to inflate and deflate one or more airbags 11 as necessary to provide the desired massage characteristics. In some embodiments, the airbags 11 may be controllable by the user to provide a more intense or less intense massage (i.e., manual or automatic). In some embodiments, the user may control and/or customize massage characteristics by user input through an application installed on a user device 51, shown in FIG. 4C, such as a mobile device, tablet, computer, or the like, which may optionally be in communication with the controller 15. In some embodiments, the user may customize one or more levels of inflation and/or deflation of airbags 11, including a pressure or amount of air applied, time durations, which airbags to inflate or deflate in different locations in the chair, and the like, through the user device. In the illustrated example, each support 4 is located between a respective one of the percussive massage heads 3 and the shaft 37. Thus, as the airbag 11 is inflated to drive the percussive massage head 3 away from the platform 24, the percussive massage head 3 protrudes further relative to the corresponding support 4 and, if the chair 10 is occupied, presses harder against the user. The proportion of the user's weight that rests on the supports 4 or the percussive massage heads 3, and the intensity of the percussive massage, can therefore be adjusted by inflating or deflating the airbag 11. The drawings and the foregoing description only relate to certain examples, however, and other arrangements may be used to enable the relative prominence of the percussive massage heads 3 and the supports 4 to be adjusted in other examples.

In some embodiments, the percussive massage heads 3 may include the force meter or force determination disclosed in U.S. Pat. No. 10,940,081, the entirety of which is incorporated by reference herein. For example, the controller 15 may have a lookup table correlating power usage values to force outputs, and may use measured power output to determine the force applied by the percussive massage heads 3. The force meter or force determination can be used in conjunction with the control of the airbag 11 and the support mechanism described herein by adjusting the prominence of the percussive massage heads 3 relative to the supports 4 until the force indicated by the force meter reaches an intended value. That is, if the force meter indicates a force above the intended value is being applied, the airbag 11 may be deflated so that the percussive massage heads 3 become less prominent relative to the supports 4, and if the force meter indicates a force below the intended value is being applied, the airbag 11 may be inflated so that the percussive massage heads 3 become more prominent relative to the supports. In some embodiments, the force meter in the percussive massage assembly may be configured to perform force measurements, and the controller 15 coupled to the percussive massage assembly may be configured to receive the force measurements from the force meter and control operation of the airbags 11 (e.g., inflating and/or deflating the airbags by predetermined amounts) and/or components of the percussive massage assembly to adjust the force applied by the percussive massage assembly. In some embodiments, the controller 15 coupled to the percussive massage assembly may provide one or more signals that control operation of the airbags 11 and/or components of the percussive massage assembly in order to adjust the pressure applied to the user based on user preferences and user needs. In some embodiments, the controller 15 may adjust the operation of the airbags 11 and/or components of the percussive massage assembly through a closed-loop algorithm using force meter measurements and user preferences for different pressure levels to be applied in different areas of the user's body (e.g., higher pressure in lower body parts, such as legs, calves, glutes, and the like, and lower pressure in upper body parts such as neck, shoulders, arms, and the like).

In some embodiments, the kneading massage heads or members 2 are similar to a massage roller that provides superficial tissue massage. In some embodiments, the percussive massage head 3 or assembly includes a percussive or reciprocating shaft 33 with variable speed and uses a pressure sensor to adjust the intensity of the massage. The percussive massage assembly can use any of the parts or components disclosed in the '307 publication, such as the motor, reciprocating assembly, etc. In some embodiments, the attachment or head on the end of the reciprocating shaft 33 of the percussive massage assembly is removable and replaceable and can include interchangeable massage heads, attachments, or treatment members.

It will be appreciated that for the percussive massage to be effective, the massage head 3 must be able to reciprocate toward and away from the user. Therefore, the weight of the user must at least partially be supported to allow the percussive massage head 3 to reciprocate. The full weight of the user on the percussive massage head 3 may prevent the massage head from being able to reciprocate (e.g., the stall force of the reciprocating motor 35 may be exceeded). Thus, in order to allow for proper reciprocation of the percussive massage head, one or more support mechanisms or support members 4 are provided to support the weight of the user. In some embodiments, the one or more support mechanisms or support members 4 may serve as a reference so that the percussive massage assembly may provide only the necessary force on the user's body. The reciprocating massage head 3 has a stroke length or amplitude, which includes a top (where the massage head is contacting the user (or the layers(s) of the chair that the user is resting against)) and a bottom (where the massage head is not contacting the user or has pulled back or away from the user). In some embodiments, the forward surface of the support member 4 is closer to the user, or more prominent, than the position of the front surface of the massage head 3 when the massage head 3 is at the bottom of its stroke. It will be appreciated that when the percussive massage arm or head is working or reciprocating, the support member(s) 4 can support the user's body weight to reduce pressure on the percussive massage assembly.

Figure 2D:
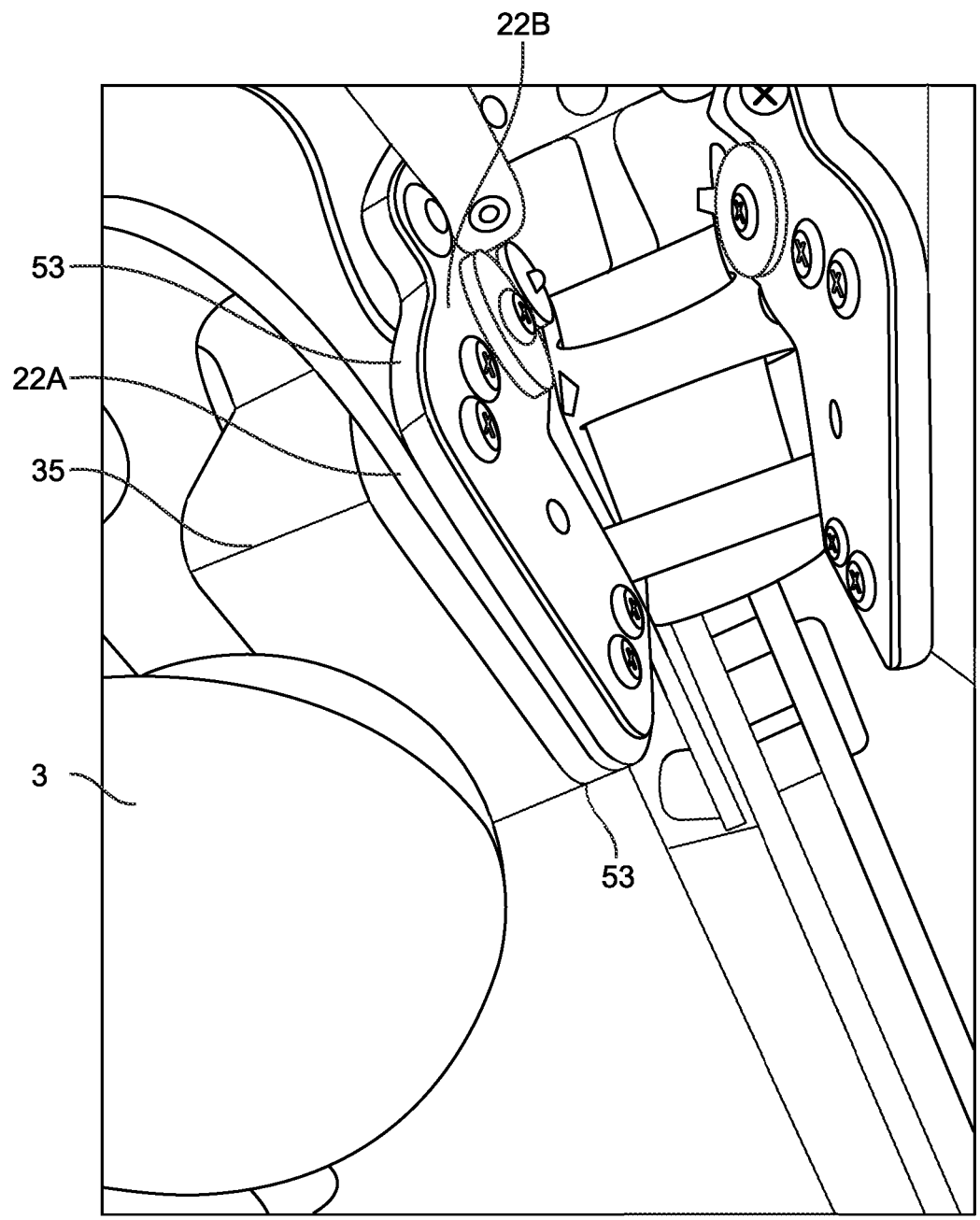
FIG. 2D is an enlarged view of a constructional detail of the carriage of FIG. 2A.

FIG. 2D is an enlarged view of where an oscillating motor 35 is attached to the carriage frame 22. An optional damping insert 53 is trapped between the oscillating motor 35 and a first plate 22A of the carriage frame 22, and another optional damping insert 53 is trapped between the first plate 22A and a second plate 22B of the carriage frame 22 that connects the first plate 22A to the platform 24. The damping insert 53 can be any material suitable for damping vibration, such as silicone rubber or a similar polymer. The oscillating motors 35 are the most significant source of vibration in the chair 10, so the damping inserts 53 located between the oscillating motors 35 and the platform 24 significantly reduce the overall vibration of the chair 10 by isolating the oscillating motors 35 from the rest of the chair 10. The damping inserts 53 cooperate with the pads 61 to create a chain of damping between the oscillating motors 35 and the floor, thereby reducing noise created by the chair 10 when the oscillating motors 35 are active.

Figure 3B:
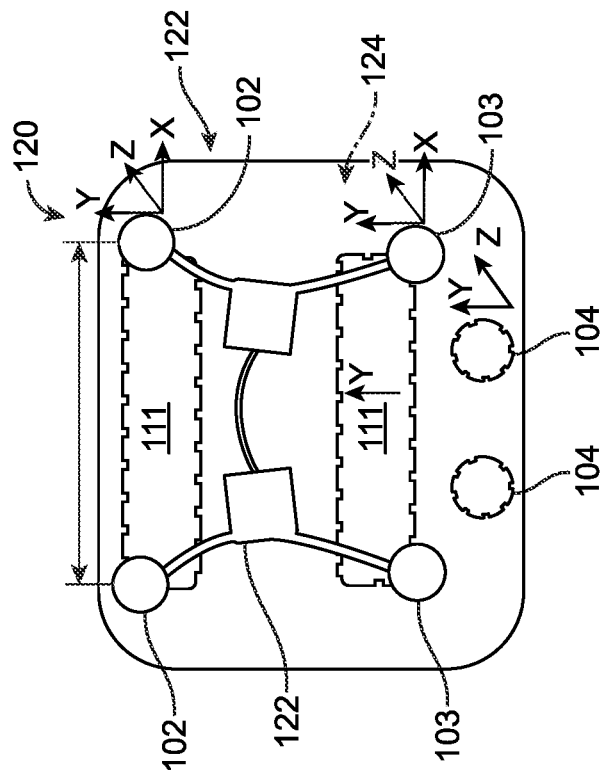
FIG. 3B is a top plan view of the carriage of FIG. 3A.
Figure 3A:
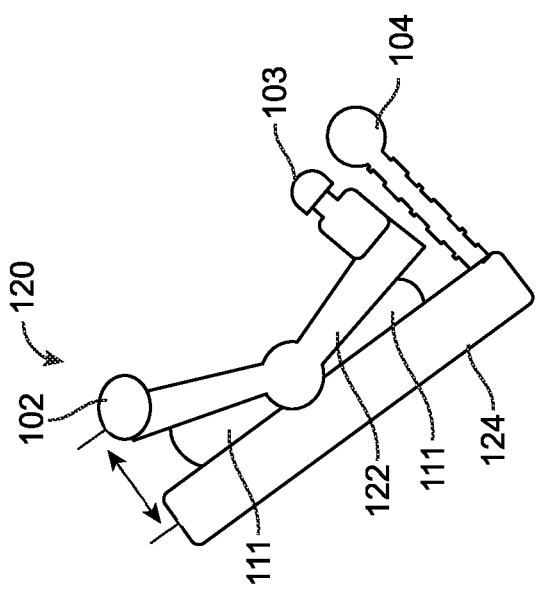
FIG. 3A is a side elevation view of a carriage according to another aspect of the present disclosure.

FIGS. 3A and 3B illustrate a massage carriage 120 according to another arrangement. The massage carriage 120 is alike to the massage carriage 20 described above except for specifically described or illustrated differences, and can therefore be included in the chair 10 instead of or in addition to the massage carriage 20. The massage carriage 120 includes two support members or mechanism 4 is represented by two shafts 4 in FIG. 2. However, in some embodiments, the support mechanism has a large surface area so that it is comfortable for the user to rest on and so that regardless of the inclination. The pressure on the percussive massage assembly is controlled. In some embodiments, the support member 4 may be embodied in any shape or configuration with a predetermined surface area that is selected for user's comfort with the percussive massage assembly. While only two shafts 4 are shown in FIGS. 3A and 3B for reference, the massage carriage 20 may include any number of support members 4 configured to support the weight of a user in the massage chair.

In some embodiments, the kneading massage heads 102 (s) and the percussive massage heads 103 can be adjusted independently or together and can move up, down, side to side or diagonally in directions indicated by the X, Y, and Z axes in FIG. 3B, with Z axes extending out of the page toward the viewer. The massage heads 103 can move with the remainder of the carriage or can move independently of or with respect to the carriage. The kneading massage heads 2 and percussive massage heads 3 can be adjusted in all of the same directions. In other embodiments, more than one carriage can be included, and carriages can be included for other body parts (e.g., the arms).

Figure 4A:
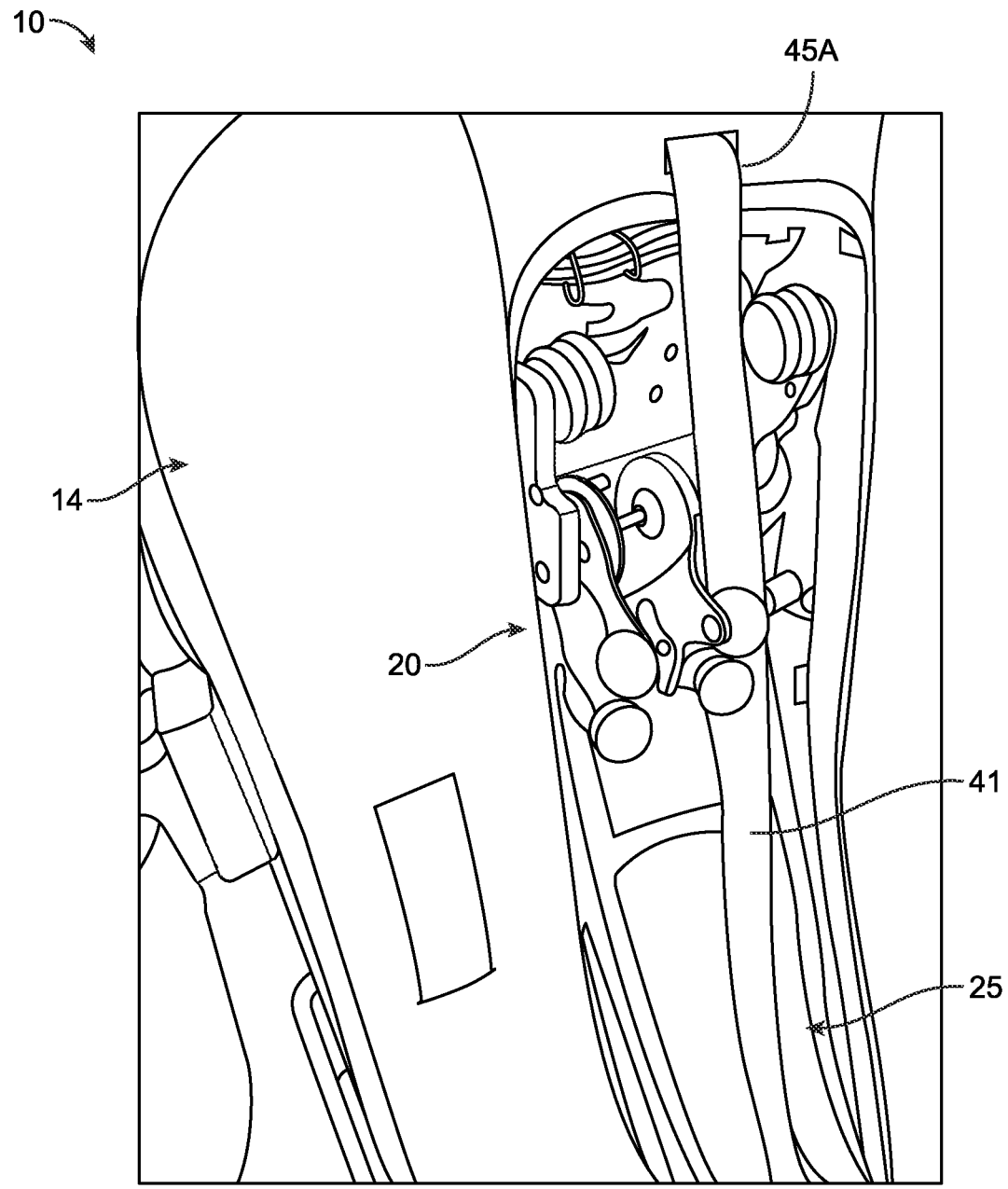
FIG. 4A illustrates a back portion of a chair including the frame of FIG. 1A in a partially disassembled state.
Figure 4B:
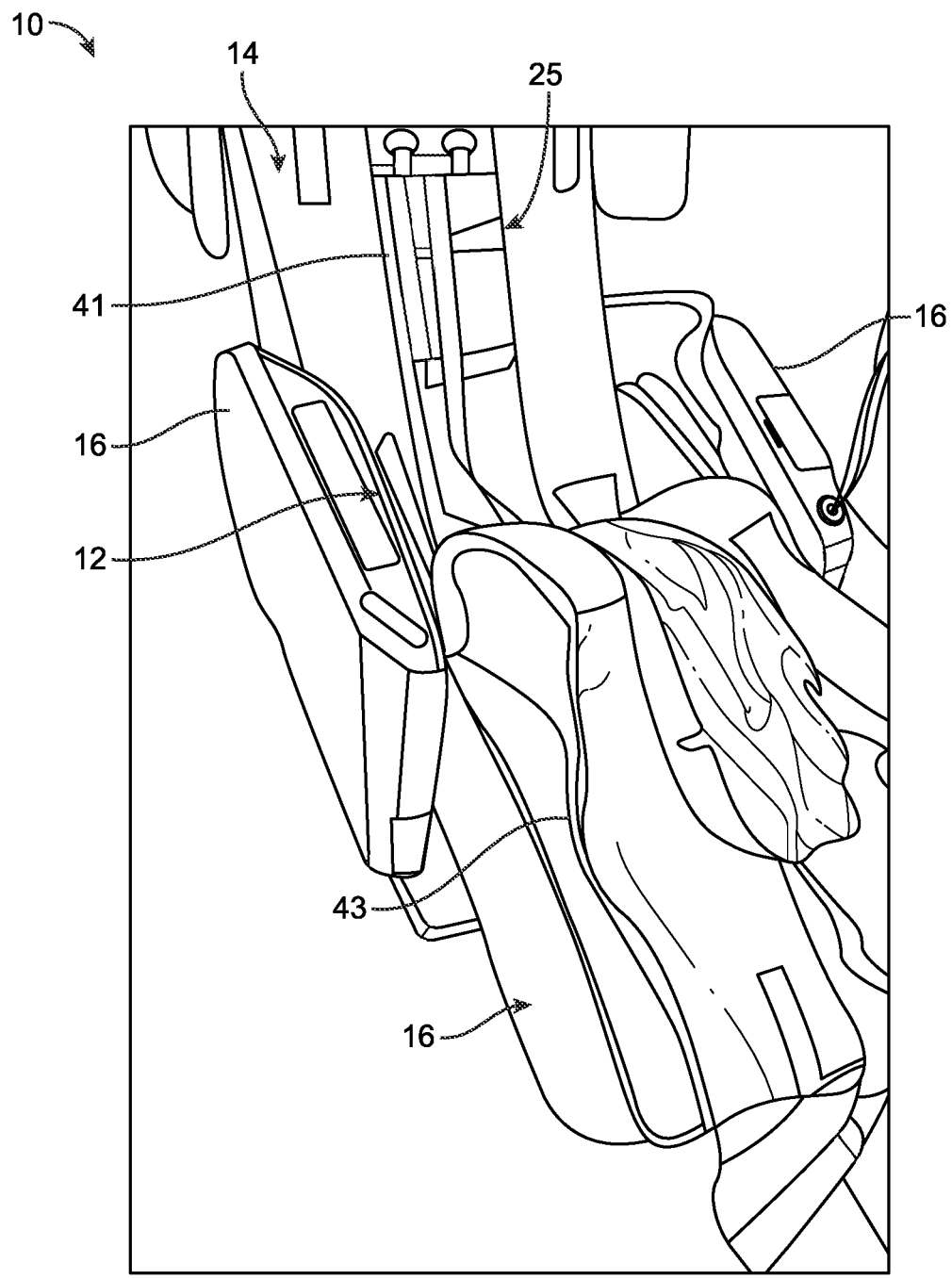
FIG. 4B illustrates the back portion, a seat portion, a leg portion, and an arm portion of the chair of FIG. 4A in the partially disassembled state.
Figure 4C:
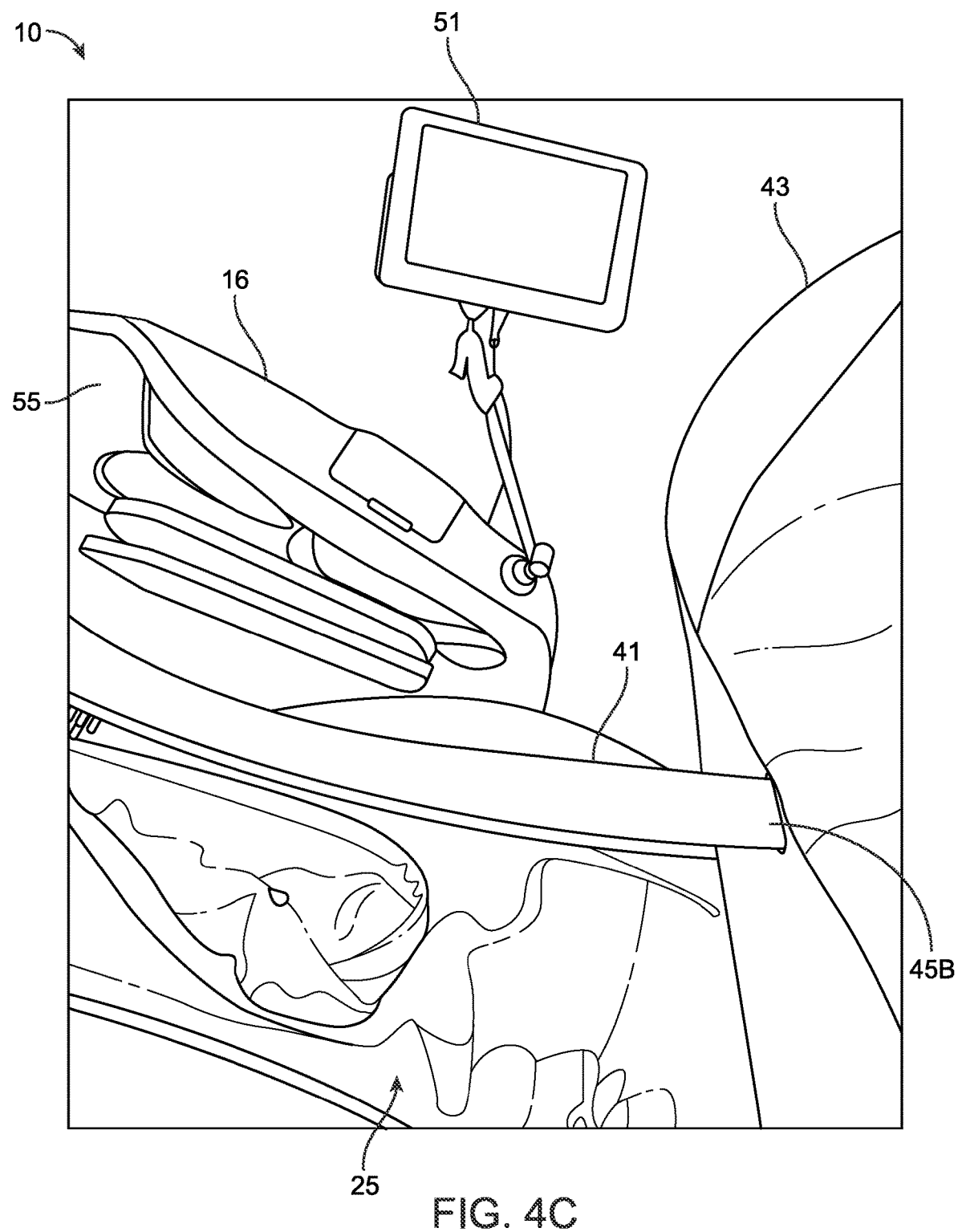
FIG. 4C is an enlarged view of a constructional detail of the chair of FIG. 4A.

As shown in FIG. 4A-4C, the chair 10 may include a support strap 41 to assist the supports 4 in bearing the weight of the user. The support strap 41 hangs in the cavity 25 and thus prevents the user from sinking into the cavity or applying too much weight to the percussive massage heads 3. The support strap 41 may have an adjustable tension. In the illustrated arrangement, the support strap 41 extends from an upper end 45A connected to the chair frame 26 to a lower end 45B connected to a removable cover 43, but in various other arrangements either or both ends of the support strap 41 may be connected to the chair frame 26 or one or more removable covers.

Figure 4D:
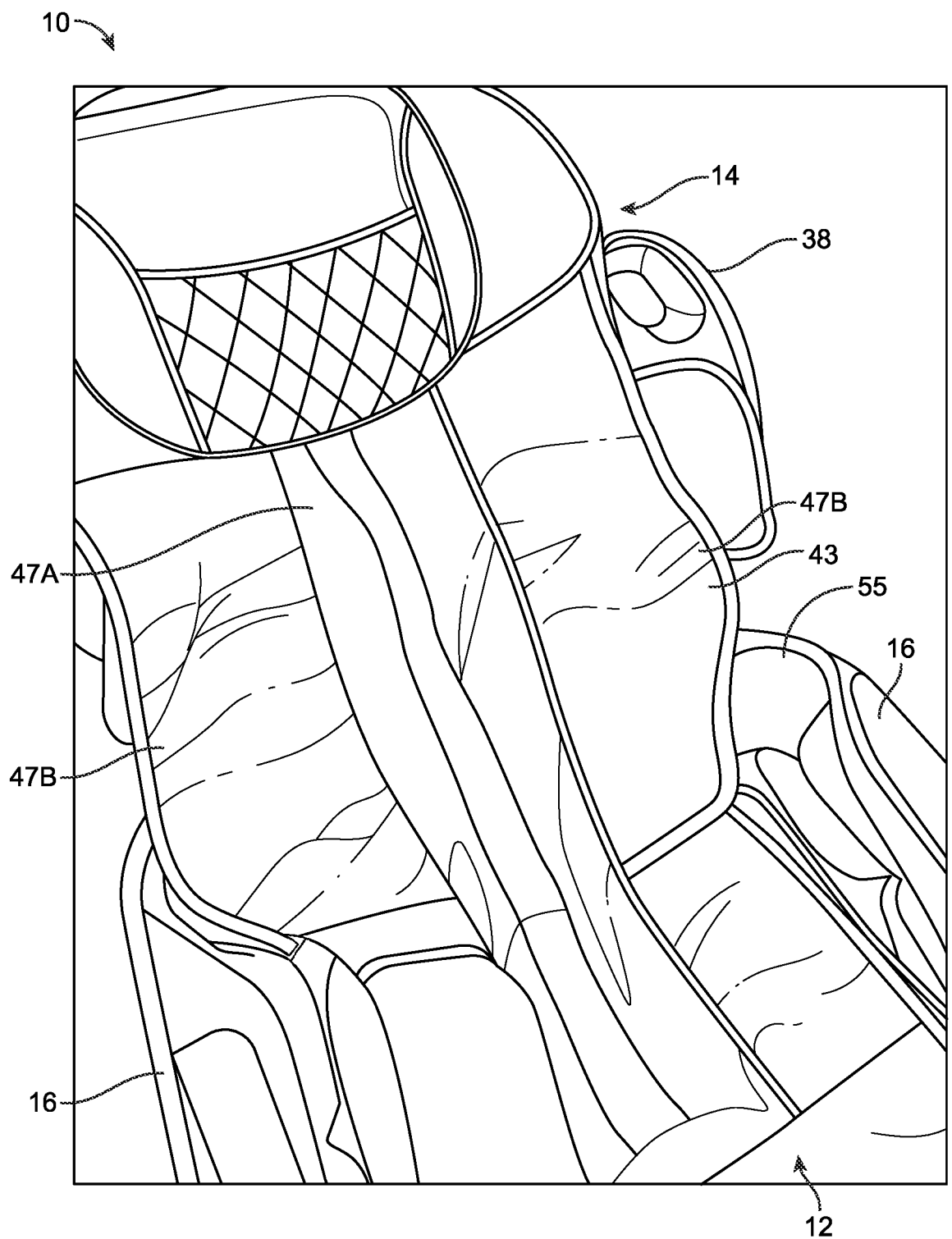
FIG. 4D illustrates the chair of FIG. 4A in an assembled state.

The removable cover 43 is removable to allow access to the cavity 25, such as for maintenance or replacement of parts, and is attachable to the chair frame 26 to complete the chair 10 and cover the cavity 25 as shown in FIG. 4D. The removable cover 43 may be attachable to the chair frame 26 by zipper, hook and loop fastening, magnets, buttons, or any other mechanism. The removable cover 43 may optionally also be coupled to the chair 10 by the support strap 41.

The removable cover 43 may be made from materials that are relatively resistant to heat and friction to avoid being damaged by the percussive massage assemblies on the massage carriage 20, such as lycra or similar fabrics, durable foams, or a combination of the two. For example, a center portion 47A of the removable cover 45 may be a thin layer of lycra or a similar fabric, while lateral portions 47B of the removable cover 45 may be thick foam cushions. In such examples, the thin material of the center portion 47A will dissipate heat quickly and provide minimal damping between the percussive massage assemblies and the user, while the thicker material of the lateral portions 47B will be durable and comfortable.

Figure 5A:
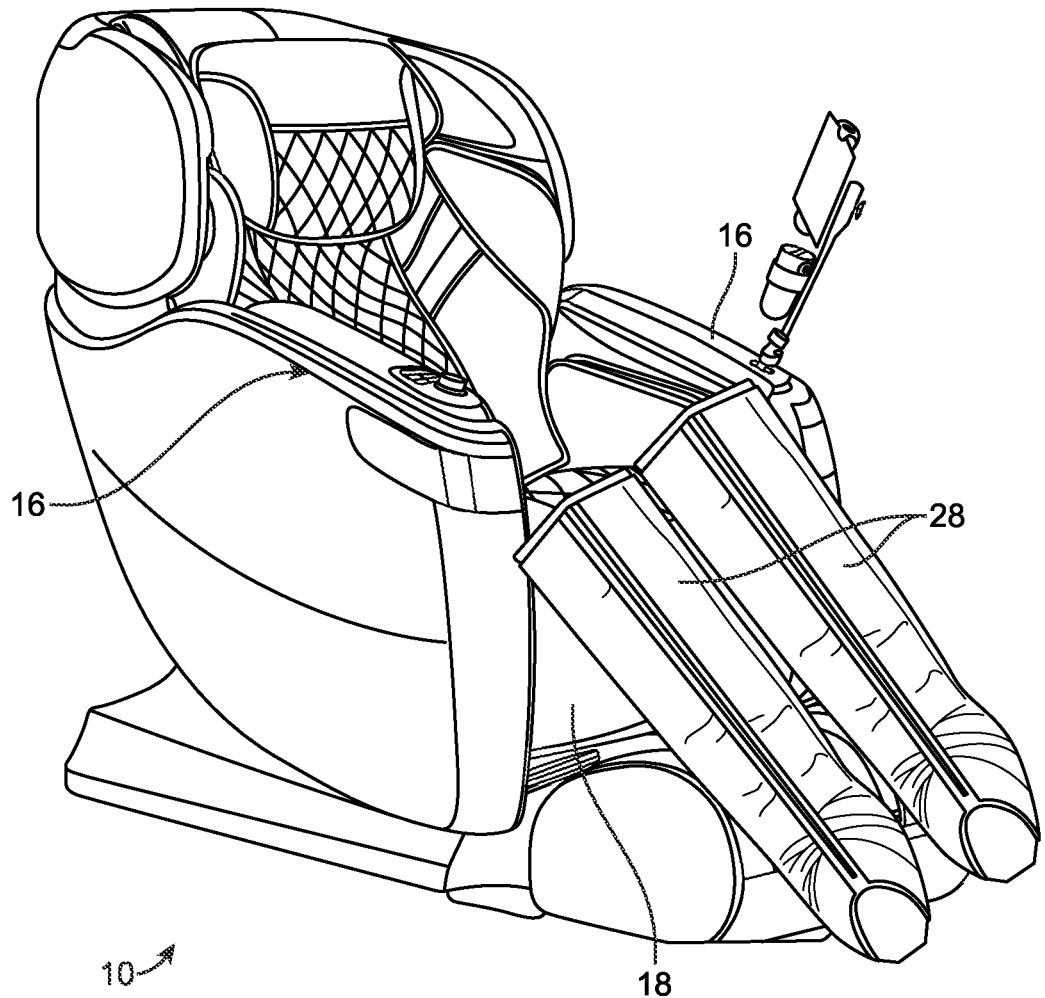
FIG. 5A illustrates the chair of FIG. 4A with external leg compression devices.
Figure 5B:
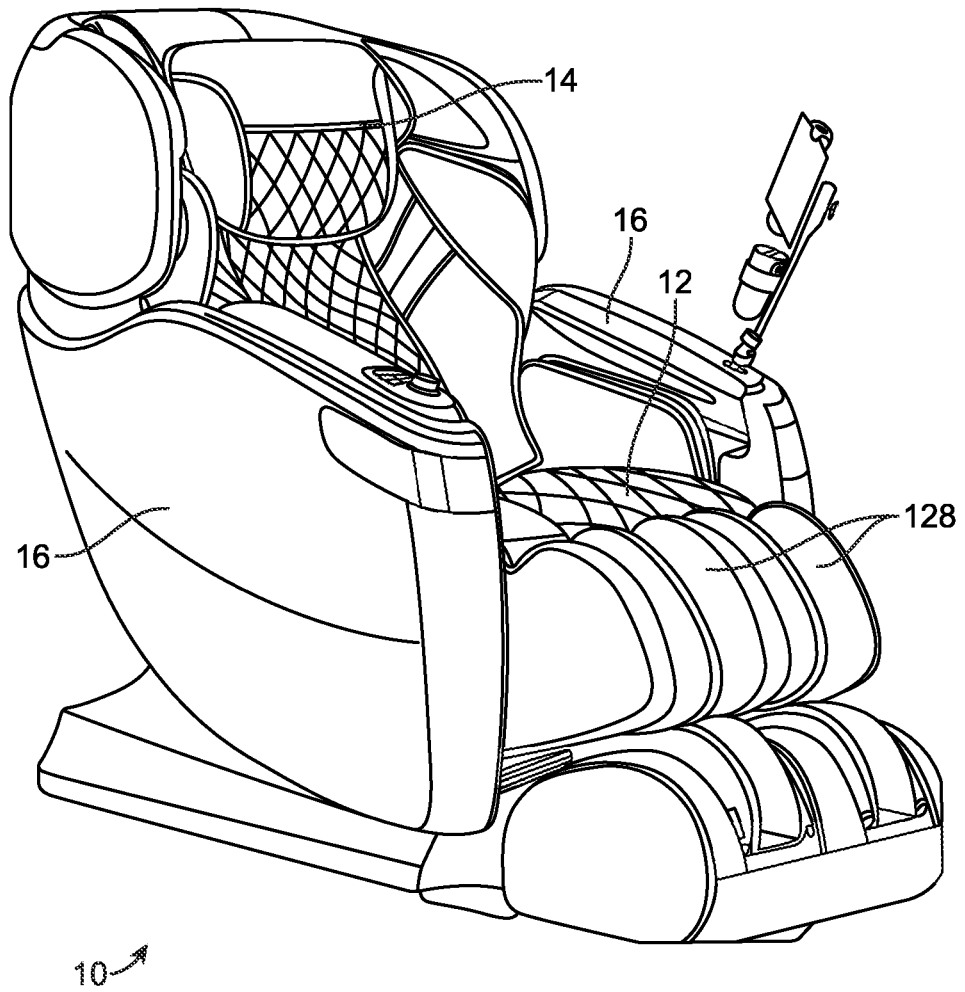
FIG. 5B illustrates a chair including integrated leg compression devices according to another aspect of the present disclosure.

The chair 10 includes pneumatic arm compressors 55 integrated into the arm portions 16, though in other examples the pneumatic arm compressors 55 may be separate from the arm portions 16 or omitted altogether. Similar, external pneumatic leg compression devices 28 are illustrated in FIG. 5A, while integrated leg compression devices 128 are illustrated in FIG. 5B. In some embodiments, the compression provided by the pneumatic compression devices or assemblies starts at the user's foot (further from the heart) and moves sequentially upwardly toward the upper leg of the user (closer to the heart). This negative gradient helps move blood toward the user's heart. Return of the blood to the heart can help with recovery, e.g., after exercise or strenuous activity. In some embodiments, the arm and/or leg pneumatic compression assemblies are modular and can be removable. This allows the user to obtain a percussive and/or kneading massage and then attach the pneumatic compression device or assembly for the legs so that they can obtain a pneumatic compression treatment. In some embodiments, the pneumatic compression assemblies are permanently attached.

For the pneumatic compression assemblies for the arms, in some embodiments, the compression can be applied to the entire arm (forearm and upper arm). In another embodiment, the compression may only be applied to one of the forearm or the upper arm.

For the pneumatic compression assemblies for the legs, in some embodiments, the compression can be applied to the entire leg—the lower leg (below the knee) and upper leg (above the knee). In another embodiment, the compression may only be applied to one of the lower leg or the upper leg. The pump(s) can be integrated into or located within the chair body or the frame thereof.

Figure 6A:
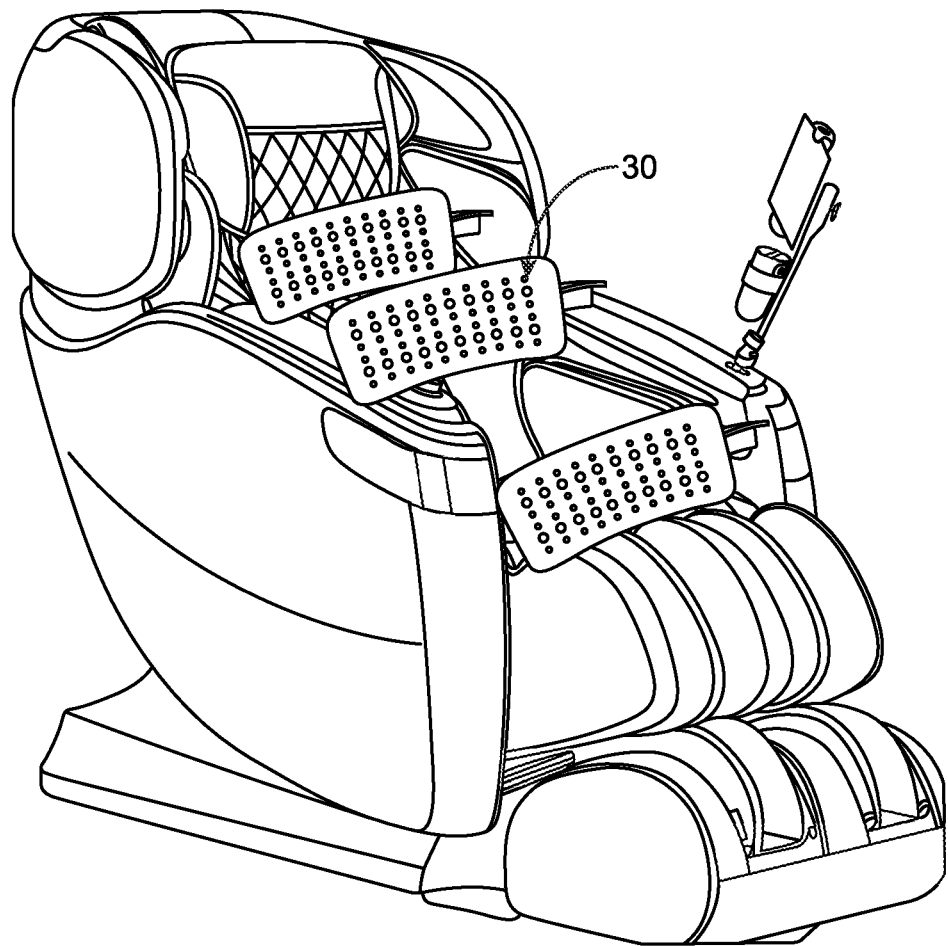
FIG. 6A illustrates the chair of FIG. 4A or 5B with far infrared panels.
Figure 6B:
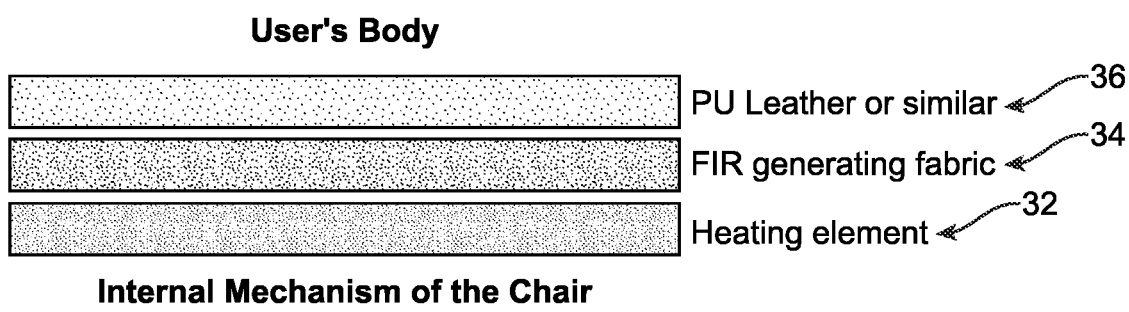
FIG. 6B is a cross-sectional view of a far infrared panel of FIG. 6A.

As shown in FIGS. 6A and 6B, in some embodiments, the chair 10 may include one or more far infrared (FIR) elements configured to provide heat or FIR therapy to a user during, before, or after a massage. In some embodiments, the chair includes an active light-emitting diode (LED) system throughout the back portion or other portions of the chair that may include one or more LEDs or LED portions 30, such as those shown in FIG. 6A, which may be FIR LEDs. In some embodiments, the LED portions 30 may be referred to herein as LED pads that are integrated in the chair. In some embodiments, the chair may include a passive system with a heated or heating element 32 and a far infrared generating or reflecting fabric layer 34 integrated into the chair (e.g., on the back portion, seat portion and/or leg and arm portions), as shown in FIG. 6B. The far infrared layer 34 may be covered by an outer layer 36 that is comfortable for the user, e.g., a polyurethane leather or other fabric as shown in FIG. 6B. It will be appreciated that the heating element or layer 32 can be used to charge the FIR layer 34. In some embodiments, a combination of LEDs and FIR generating fabric can be used to provide heat to the user in the chair. The active LED portions 30 can include a member that has a plurality of LEDs mounted thereon and that is embedded or mounted in or on the chair (e.g., in the outer layer). In some embodiments, a user of the chair may control operation of the one or more of the active LED portions 30, heating elements 32, and/or the FIR generating fabric 34 by user input through an application installed on a user device such as a mobile device, tablet, computer, or the like.

In some embodiments, the path followed by the percussive massage head(s) and kneading massage (heads) does not include any of the FIR LEDs or heating element(s)/FIR fabric) such that the LEDs, heating element or FIR fabric are not damaged by the massage heads. Therefore, in some embodiments, the chair includes FIR specific areas where there is no massage therapy. In another embodiment, the FIR areas may overlap with the massage therapy areas. In some embodiments, the chair may include a first region comprising the percussive massage head(s) and kneading massage (heads), and a second region comprising the FIR LEDs and/or heating element(s)/FIR fabric, wherein there is minimal overlap between the first and second regions of the massage chair in order to prevent damage to the different components.

Figure 7:
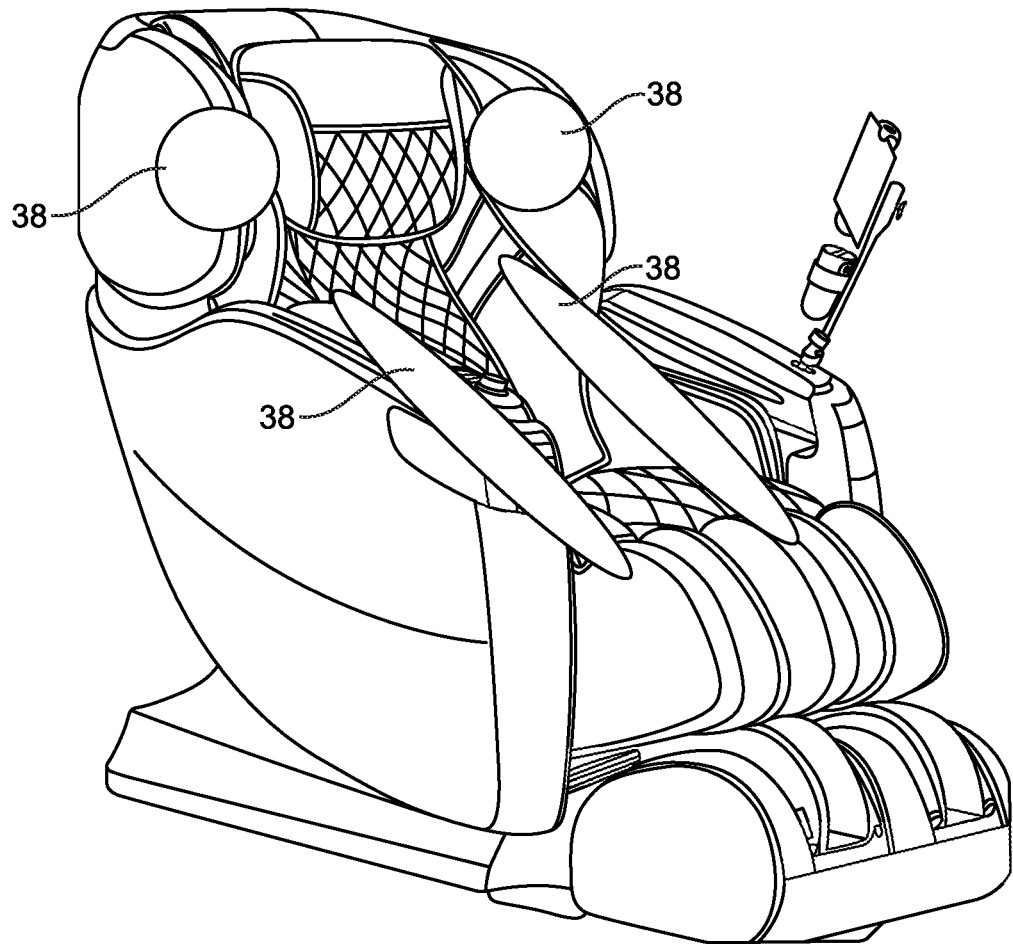
FIG. 7 illustrates the chair of FIG. 4A or 5B with integrated haptic speakers.

As shown in FIG. 7, in some embodiments, the chair 10 may be configured to provide sound therapy through one or more speakers 38 and/or components integrated in the chair. In some embodiments, the sound is or includes haptic sound (e.g., sound that can be felt by the user) that is directed through speakers 38. FIG. 7 shows exemplary positioning of speakers 38. However, speakers can be included anywhere within the chair. In some embodiments, the haptic sound or changes thereto are related to the percussive therapy and/or changes thereto. As a result, the frequency, force and position of the one or more percussive massage heads in the chair can help the user experience the therapeutic session in a multisensory way, which may facilitate entry into a meditative state. For example, during a recovery session, the frequency of one or more percussive massage heads may go from a higher frequency value to a lower frequency value to help promote relaxation as the sounds (output by one or more speakers 38 in the chair) in the meditation session (and or the sensations delivered haptically) reduce in pitch (i.e., down in sound frequency). In short, the haptic sound is correlated to one or more of the frequency, amplitude, force or position of the percussive massage device or therapy provided in the chair. Sound therapy generates or provides different wavelengths to a user of the chair to provide different reactions or sensations in the body and/or mind. Correlating these to the percussive therapy (and possibly the other technologies described herein, such as the pneumatic compression), as provided through the chair, may be advantageous. In some embodiments, a user of the chair may control operation of the one or more of the speakers by user input through an application installed on a user device such as a mobile device, tablet, computer, or the like. In some embodiments, the user of the chair may be able to access preselected, customized sounds or music that is recommended through an application that utilizes an intelligence engine to provide recommendations to the user.

Any type of sound generator or vibrating device can be used for generating haptic sound. In some embodiments, the haptic vibrations are provided via vibration devices such as those taught in U.S. patent application Ser. No. 17/406,478, filed Aug. 19, 2021, the entirety of which is incorporated by reference herein. The vibration devices can be distributed throughout the chair and the outer layer thereof so that the user can feel the vibrations created thereby.

In some embodiments, the positioning of the user in the chair is adjustable. For example, the leg portions can pivot upwardly and downwardly and/or the entire chair can rotate about a horizontal axis so that the user lies generally flat (i.e., the heart of the user is generally at the same level as the legs in a horizontal plane).

In some embodiments, the chair includes one or more sensors, actuators, or devices configured to sense and/or capture biometric data of the user (e.g., heart rate, heart rate variability, temperature, blood oxygenation, etc.) so that a determination can be made about the user's health level, etc. The chair and/or the controller 15 and software associated therewith can make or provide recommendations to the user (based on biometric data collected by sensors integrated in the chair and/or biometric data collected by third party providers) on what type of recovery session (e.g., which of the features of the chair to be utilized) may be beneficial. U.S. Patent Publication No. 2021/0059898, the entirety of which is incorporated herein by reference, teaches the collection of various biometric data. Different recovery routines or protocols can be programmed into the chair. These routines may or may not be based on the biometrics discussed herein. A software application or "app" can be used with the chair, and the application may be installed on a user device such as a mobile device, tablet, computer, or the like. In some embodiments, the user device may be removably attached to the chair or separate from the chair. In some embodiments, the user device may be communicatively coupled to a controller 15 associated with the chair, wherein the controller is configured to operate various components and perform the functions and features of the chairs as described herein. In some embodiments, any of the chairs or other massage furniture of the present disclosure may include one or more biometric sensors, including but not limited to a heart rate sensor, an eye motion sensor, a microphone, a blood pressure sensor, an electroencephalogram sensor, a muscle activity sensor, an electrocardiography sensor, a photoplethysmography sensor, an electroencephalograph sensor, and accelerometer, a pressure sensor, and/or a touch sensor.

The percussive massage assemblies 90 on the carriage 20 may each individually be alike to one of the reciprocating massage devices shown in U.S. Pat. No. 10,945,915, filed Mar. 19, 2020, or U.S. Pat. No. 11,160,723, filed Mar. 3, 2021, the entireties of which are hereby incorporated herein by reference, except for optional differences in housing shape or optional provision of power by external power supplies instead of the internal batteries of the devices in the '915 and '723 Patents.

Figure 8A:
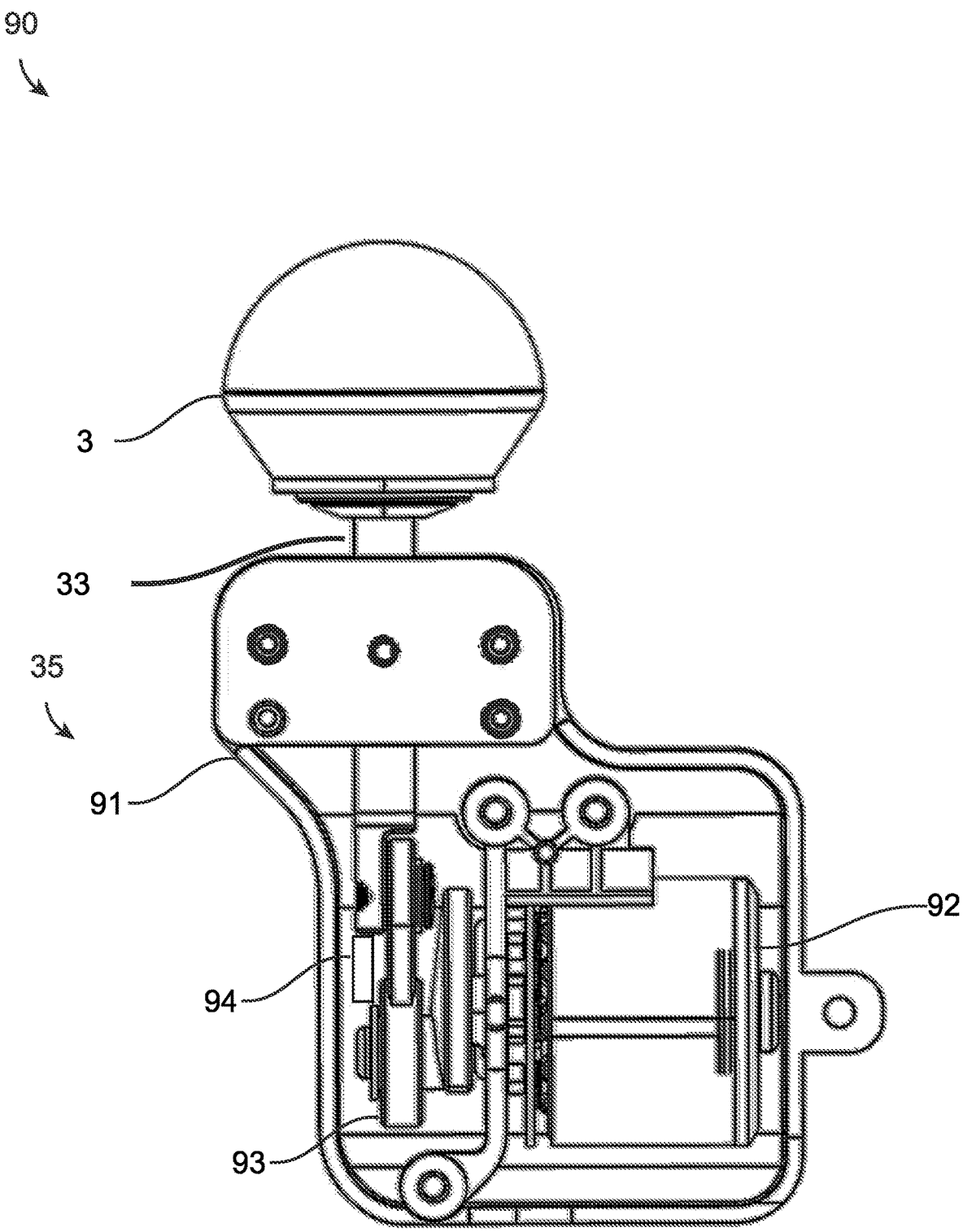
FIG. 8A is a side elevation view of a reciprocating massage assembly of the carriage of FIG. 2A.
Figure 8B:
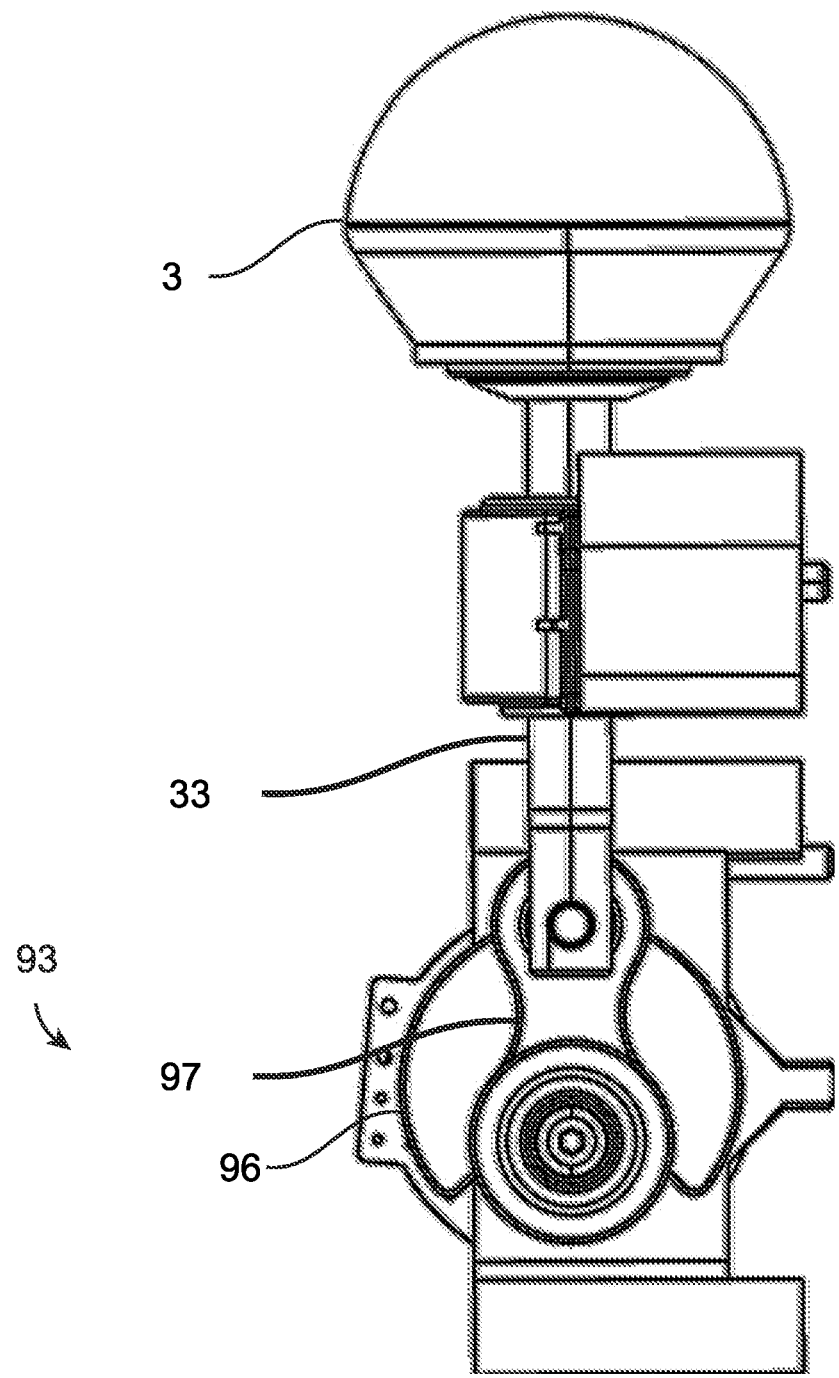
FIG. 8B is a front elevation view of internal components of the assembly of FIG. 8B.

Some details of an example arrangement of the reciprocating massage assemblies 90 of the present disclosure are shown in FIGS. 8A and 8B. Each reciprocating massage assembly 90 includes a housing 91 that defines a housing interior in which a motor 92 and a rotating assembly 93 are located. The motor 92 generates torque along a motor axis about which the motor 92 drives the rotating assembly 93 to rotate. The rotating assembly 93 thus rotates on a reciprocation plane on which a thickness of the housing 91 is defined. The motor 92 is located entirely on one side of the reciprocation plane The rotating assembly 93 includes an arm 97 that is hingedly connected at one end to the shaft 33 and at another end to the motor 92. The end of the arm 97 connected to the motor 92 is offset from the motor axis, so driving the rotating assembly 93 to rotate about the motor axis causes the shaft 33 to reciprocate linearly along a reciprocating axis. The rotating assembly 93 may include a counterweight 96 that also rotates about the motor axis to reduce the vibration of the percussive massage assembly 90 during operation.

An optional battery 94 may be enclosed in the housing 91. The battery 94 may extend along a battery axis parallel to the shaft 33 and the reciprocation plane, and thus normal to the motor axis. The battery 94 is located on an opposite side of the reciprocation plane from the motor 92.

Though the chairs of the present disclosure are illustrated in the figures as having the form factor of a home recliner, the concepts of the present disclosure are equally applicable to automobile seats, airplane seats, seats for railway cars, transport chairs, vehicle seats, seats for transportation, car seats, seat cushions, or seat pads as well beds, mattresses, futon mattresses, spring mattresses, mattress foundations, mattress toppers, pillows and bolsters, sofas, recliners, chairs, booster seats, or massage tables.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present disclosure. Other measurements or dimensions are within the scope of the disclosure.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the disclosure have been shown and described, it is to be understood that all the terms used herein are descriptive rather than limiting, and that many changes, modifications, and substitutions may be made by one having ordinary skill in the art without departing from the spirit and scope of the disclosure.

What is claimed is:

1. A massage chair comprising:
    a seat portion;
    a back portion;
    a leg portion; and
    a massage carriage configured to move within the seat portion, the back portion, and the leg portion, wherein the massage carriage comprises:
        a percussive massage assembly comprising a motor, a reciprocating shaft coupled to the motor and configured to reciprocate linearly along a reciprocation axis in response to activation of the motor, and a reciprocating massage head coupled to the reciprocating shaft; and
        a support mechanism associated with the percussive massage assembly, wherein the support mechanism is configured to support a weight of a user of the massage chair, thereby allowing the reciprocating shaft and the reciprocating massage head of the percussive massage assembly to reciprocate; and wherein:
    the percussive massage assembly is mounted on the massage carriage such that the reciprocating massage head is configured to reciprocate linearly between a first position and a second position, wherein the first position is more prominent from a platform of the massage carriage than the second position, and
    the support mechanism is mounted to the massage carriage and includes a wheel that is less prominent from the platform than the first position of the reciprocating massage head and more prominent from the platform than the second position of the reciprocating massage head.

2. The massage chair of claim 1, wherein the leg portion includes at least a first leg pneumatic compression assembly.

3. The massage chair of claim 1, further comprising: first and second arm portions, wherein the first arm portion includes a first arm pneumatic compression assembly, and wherein the second arm portion includes a second arm pneumatic compression assembly.

4. The massage chair of claim 3, wherein the first and second pneumatic compression assemblies are removable from the first and second arm portions.

5. The massage chair of claim 1, further comprising: one or more far infrared (FIR) elements configured to provide FIR therapy to the user of the massage chair.

6. The massage chair of claim 5, wherein the one or more FIR elements comprises at least one of a far infrared fabric and far infrared light emitters.

7. The massage chair of claim 1, wherein the percussive massage assembly is mounted on the massage carriage, and wherein the massage carriage further comprises a kneading massage assembly.

8. The massage chair of claim 1, wherein one or more movements and operations of components in the massage carriage are controlled by a controller coupled to the massage chair.

9. The massage chair of claim 8, wherein the controller coupled to the massage chair is operated by the user of the massage chair by providing user input via an application installed on a user device of the user.

10. The massage chair of claim 1, further comprising: one or more dampeners arranged between portions of the massage carriage and the percussive massage assembly, wherein the one or more dampeners are configured to dampen one or more vibrations generated by the motor of the percussive massage assembly.

11. The massage chair of claim 1, further comprising:
a frame underneath the seat, the leg, and the back portions;
one or more tracks coupled to the frame, wherein the massage carriage is configured to move along the one or more tracks.

12. The massage chair of claim 11, further comprising:
one or more dampeners arranged between the one or more tracks and the frame, wherein the one or more dampeners are configured to dampen one or more vibrations generated by movement of the massage carriage along the one or more tracks.

13. The massage chair of claim 11, further comprising:
a central cavity below the seat, the leg, and the back portions, wherein the central cavity is configured to house the frame, the one or more tracks, and the massage carriage.

14. The massage chair of claim 11, further comprising:
a cover arranged over the central cavity; and
a support strap, wherein the cover is coupled to the massage chair by the support strap.

15. The massage chair of claim 14, wherein a first end of the support strap is attached to an interior surface of the cover, and a second end of the support strap is attached to the back portion of the massage chair.

16. The massage chair of claim 13, comprising a support strap that hangs in the cavity and is configured to prevent a user from sinking into the cavity.

17. A massage chair comprising:
a back portion; and
a massage carriage configured to move within the back portion, wherein the massage carriage comprises:
a platform;
a frame pivotably mounted to the platform and including a first end and a second end, the first end being movable relative to the platform independently of the second end and the second end being movable relative to the platform independently of the first end;
a percussive massage assembly mounted to the first end of frame and comprising a motor, a reciprocating shaft coupled to the motor and configured to reciprocate linearly along a reciprocation axis in response to activation of the motor, and a reciprocating massage head coupled to the reciprocating shaft;
a kneading massage head mounted to the second end of the frame; and
a first airbag located between the first end of the frame and the platform and a second airbag located between the second end of the frame and the platform, wherein the massage carriage is configured such that the prominence of the percussive massage assembly relative to the platform and the prominence of the kneading massage head relative to the platform can be independently adjusted by inflating the first airbag or the second airbag to either move the first end relative to the platform without affecting the position of the second end or move the second end relative to the platform without affecting the position of the first end.

18. A massage chair comprising:
a seat portion;
a back portion;
a leg portion; and
a massage carriage configured to move within the seat portion, the back portion, and the leg portion, wherein the massage carriage comprises:
a platform;
a frame that is pivotably mounted to the platform and that includes an end that is biased away from the platform;
a percussive massage assembly mounted to the end of frame and comprising a motor, a reciprocating shaft coupled to the motor and configured to reciprocate linearly along a reciprocation axis in response to activation of the motor, and a reciprocating massage head coupled to the reciprocating shaft; and
a support mechanism mounted to the frame, wherein the support mechanism comprises a wheel and is configured to support a weight of a user of the massage chair, thereby allowing the reciprocating shaft and the reciprocating massage head of the percussive massage assembly to reciprocate between a first position that is more prominent from the platform than the wheel and a second position that is less prominent from the platform than the wheel.

19. A massage chair comprising:
a seat portion;
a back portion;
a massage carriage configured to move within the back portion, wherein the massage carriage comprises:
a platform;
a frame including a first point and a second point and being pivotably mounted to the platform such that the prominence of the first point relative to the platform and the prominence of the second point relative to the platform are independently variable and the first point and the second point are biased away from the platform;
a first percussive massage assembly mounted to the first point and a second percussive massage assembly mounted to the second point, wherein each percussive massage assembly comprises a motor, a reciprocating shaft coupled to the motor and configured to reciprocate linearly along a respective reciprocation axis in response to activation of the motor, a reciprocating massage head coupled to the reciprocating shaft, and a force meter configured to measure force applied by the reciprocating massage head;

a controller configured to adjust the magnitude of the bias on the first point and the second point to bring the forces measured by the force meters toward an intended value; and a support mechanism mounted to the frame, wherein the support mechanism comprises a wheel and is configured to support a weight of a user of the massage chair, thereby allowing the reciprocating shaft and the reciprocating massage head of the percussive massage assembly to reciprocate between a first position that is more prominent from the platform than the wheel and a second position that is less prominent from the platform than the wheel.

* * * * *

UNITED STATES PATENT AND TRADEMARK OFFICE
CERTIFICATE OF CORRECTION

PATENT NO. : 11,998,504 B2
APPLICATION NO. : 17/931079
DATED : June 4, 2024
INVENTOR(S) : Sanchez Solana It is certified that error appears in the above-identified patent and that said Letters Patent is hereby corrected as shown below:

On the Title Page

On Page 2, Column 1, under Item (63) "Related U.S. Application Data", Line 7, delete "29/709,815," and insert -- 29/708,815, --, therefor.

Signed and Sealed this
Third Day of September, 2024

Katherine Kelly Vidal
*Director of the United States Patent and Trademark Office*